United States Patent
Liu et al.

(10) Patent No.: US 10,821,565 B2
(45) Date of Patent: Nov. 3, 2020

(54) METHOD OF MANUFACTURING A REMOTE-CONTROLLED MICRO-SCALE THREE-DIMENSIONAL SELF-ASSEMBLY

(71) Applicant: Regents of the University of Minnesota, Minneapolis, MN (US)

(72) Inventors: Chao Liu, Heilongjiang Province (CN); Jeong-Hyun Cho, Woodbury, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 49 days.

(21) Appl. No.: 15/997,049

(22) Filed: Jun. 4, 2018

(65) Prior Publication Data
US 2019/0366492 A1    Dec. 5, 2019

Related U.S. Application Data

(60) Provisional application No. 62/514,205, filed on Jun. 2, 2017.

(51) Int. Cl.
*B23P 19/04*    (2006.01)
*B81C 1/00*    (2006.01)
(Continued)

(52) U.S. Cl.
CPC ............. *B23P 19/04* (2013.01); *B81B 7/00* (2013.01); *B81C 1/00007* (2013.01);
(Continued)

(58) Field of Classification Search
CPC ....... B23P 19/04; B41M 7/00; B81C 1/00007; B81C 1/00134; B81C 2201/0163;
(Continued)

(56) References Cited

U.S. PATENT DOCUMENTS

| 5,190,761 A | 3/1993 | Liburdy |
| 5,643,246 A * | 7/1997 | Leeb ................... A61K 9/0009 |
| | | 128/899 |

(Continued)

FOREIGN PATENT DOCUMENTS

CN    200963827 Y    10/2007

OTHER PUBLICATIONS

J. Guan, H. He, L. J. Lee, D. J. Hansford, Fabrication of particulate Reservoir-Containing, capsulelike, and Self-Folding polymer microstructures for drug delivery. Small. 3, 412-418 (2007).
(Continued)

*Primary Examiner* — Sarang Afzali
(74) *Attorney, Agent, or Firm* — Dicke, Billig & Czaja, PLLC

(57) ABSTRACT

Methods of manufacturing a 3D micro-scale structure. A 2D net including a plurality of panels and a plurality of hinges is provided. The panels are arranged in a pattern. The hinges interconnect immediately adjacent ones of the panels within the pattern. An energy source remote from the 2D net is powered to deliver energy to the 2D net. The delivered energy triggers the 2D net to self-fold into a 3D micro-scale structure. The delivered energy creates an eddy current within at least one component of the 2D net, with the eddy current generating heat sufficient to melt at least one of the hinges. The melting hinge causes the corresponding panels to fold or pivot relative to one another. In some embodiments, the energy source is a microwave energy source. In other embodiments, the energy source delivers a magnetic field.

18 Claims, 20 Drawing Sheets

(51) Int. Cl.
  *B81B 7/00* (2006.01)
  *B82Y 15/00* (2011.01)
  *B82Y 5/00* (2011.01)
(52) U.S. Cl.
  CPC .. *B81C 1/00134* (2013.01); *B81C 2201/0163* (2013.01); *B82Y 5/00* (2013.01); *B82Y 15/00* (2013.01); *Y10S 977/882* (2013.01); *Y10S 977/90* (2013.01); *Y10S 977/901* (2013.01); *Y10S 977/904* (2013.01); *Y10S 977/906* (2013.01)
(58) Field of Classification Search
  CPC ......... B82Y 15/00; B82Y 5/00; Y10S 977/81; Y10S 977/813; Y10S 977/882; Y10S 977/90; Y10S 977/901; Y10S 977/902; Y10S 977/904; Y10S 977/905; Y10S 977/906; B81B 7/00
  See application file for complete search history.

(56) References Cited

U.S. PATENT DOCUMENTS

| | | | |
|---|---|---|---|
| 8,246,917 B2* | 8/2012 | Gracias | A61K 9/0097 422/547 |
| 8,703,073 B2* | 4/2014 | Gracias | B81B 3/0024 422/547 |
| 9,373,443 B2 | 6/2016 | Kim et al. | |
| 2004/0191321 A1 | 9/2004 | Guan et al. | |
| 2010/0326071 A1 | 12/2010 | Gracias et al. | |
| 2012/0135237 A1* | 5/2012 | Gracias | B81C 1/00007 428/402 |
| 2014/0249499 A1 | 9/2014 | Selaru et al. | |
| 2016/0106399 A1 | 4/2016 | Gracias et al. | |

OTHER PUBLICATIONS

C. Liu, J. Schauff, D. Joung, J. Cho, Remotely Controlled Microscale 3D Self-Assembly Using Microwave Energy. Advanced Materials Technologies. 2(2017).
W. Xu, Z. Qin, C. T. Chen, H. R. Kwag, Q. Ma, A. Sarkar, M. J. Buehler, D. H. Gracias, Ultrathin thermoresponsive self-folding 3D graphene. Science Advances. 3, e1701084 (2017).
J. Mu, C. Hou, H. Wang, Y. Li, Q. Zhang, M. Zhu, Origami-inspired active graphene-based paper for programmable instant self-folding walking devices. Science Advances. 1, e1500533 (2015).
Y. Liu, B. Shaw, M. D. Dickey, J. Genzer, Sequential self-folding of polymer sheets. Science Advances. 3, e1602417 (2017).
Y. V. Kalinin, J. S. Randhawa, D. H. Gracias, Three-Dimensional Chemical Patterns for Cellular Self-Organization. Angewandte Chemie International Edition. 50, 2549-2553 (2011).
W. Cui, J. Li, G. Decher, Self-Assembled Smart Nanocaniers for Targeted Drug Delivery. Adv Mater. 28, 1302-1311 (2016).
S. Semiatin, Elements of induction heating: design, control, and applications (ASM International, 1988).
J. Davies, P. Simpson, Induction heating handbook (McGraw-Hill Companies, 1979), p. 99-106.
F. Fiorillo, Characterization and measurement of magnetic materials (Academic Press, 2004), p. 1-8.
A.A. Solovev et al., "Catalytic microtubular jet engines self-propelled by accumulated gas bubbles", Small 5, 1688-1692 (2009).
A. Ghosh et al., "Controlled propulsion of artificial magnetic nanostructured propellers", Nano Letters 9, 2243-2245 (2009).
V. Garcia-Gradilla et al., "Functionalized ultrasound-propelled magnetically guided nanomotors: Toward practical biomedical applications", ACS Nano 7, 9232-9240 (2013).
V. Magdanz et al., "How to improve spermbot performance", Adv. Funct. Mater. 25, 2763-2770 (2015).
A. Legrain, "Elastocapillary self-folding of micro-machined structures", 2014, pp. 3-5.

G. M. Whitesides, B. Grzybowski, Self-assembly at all scales. Science. 295, 2418-2421 (2002).
J. G. Fernandez, A. Khademhosseini, Micro-masonry: construction of 3D structures by microscale self-assembly. Adv. Mater. 22, 2538-2541 (2010).
J. L. Silverberg, J. H. Na, A. A. Evans, B. Liu, T. C. Hull, C. D. Santangelo, R. J. Lang, R. C. Hayward, I. Cohen, Origami structures with a critical transition to bistability arising from hidden degrees of freedom. Nature Materials. 14, 389 (2015).
T. G. Leong, A. M. Zarafshar, D. H. Gracias, Three-dimensional fabrication at small size scales. Small. 6, 792-806 (2010).
C. Sung et al., "Self-folded soft robotic structures with controllable joints", IEEE ICRA, 2017, p. 580-587.
A. A. Solovev, S. Sanchez, M. Pumera, Y. F. Mei, O. G. Schmidt, Magnetic Control of Tubular Catalytic Microbots for the Transport, Assembly, and Delivery of Micro-objects. Advanced Functional Materials. 20, 2430-2435 (2010).
5. Felton, M. Tolley, E Demaine, D. Rus, R. Wood, Applied origami. A method for building self-folding machines. Science. 345, 644-646 (2014).
G. J. Hayes, Y. Liu, J. Genzer, G. Lazzi, M. D. Dickey, Self-folding origami microstrip antennas. IEEE Transactions on Antennas and Propagation. 62, 5416-5419 (2014).
P. Yang, Z. H. Lin, K. C. Pradel, L Lin, X. Li, X. Wen, J. H. He, Z. L. Wang, Paper-based origami triboelectric nanogenerators and self-powered pressure sensors. ACS Nano. 9, 901-907 (2015).
J. Cho, S. Hu, D. Gracias, Self-assembly of orthogonal three-axis sensors. Appl. Phys. Lett. 93, 043505 (2008).
E. Couturier, S. C. Du Pont, S. Douady, The filling law: A general framework for leaf folding and its consequences on leaf shape diversity. J. Theor. Biol. 289, 47-64 (2011).
L. Mahadevan, S. Rica, Self-organized origami. Science. 307, 1740 (2005).
C. Lv, D. Krishnaraju, G. Konjevod, H. Yu, H. Jiang, Origami based mechanical metamaterials. Scientific Reports. 4, 5979 (2014).
J. L. Silverberg et al., Applied origami. Using origami design principles to fold reprogrammable mechanical metamaterials. Science. 345, 647-650 (2014).
W. Y. Tsai, M. K. Chen, P. R. Wu, Y. H. Chen, T. Y. Chen, J. W. Chen, C. H. Chu, P. C. Wu, C. Y. Liao, H. Wu, H. C. Wang, Plasmonic metadevices by vertical split ring resonator, Optical MEMS and Nanophotonics (OMN), 2016 International Conference on, Singapore, Singapore, Jul. 31-Aug. 4, 2016.
R. Fernandes, D. H. Gracias, Self-folding polymeric containers for encapsulation and delivery of drugs. Adv. Drug Deliv. Rev. 64, 1579-1589 (2012).
H. He, J. Guan, J. L. Lee, An oral delivery device based on self-folding hydrogels. J. Controlled Release. 110, 339-346 (2006).
C. L. Randall, T. G. Leong, N. Bassik, D. H. Gracias, 3D lithographically fabricated nanoliter containers for drug delivery. Adv. Drug Deliv. Rev. 59, 1547-1561 (2007).
S. Erkeçoğlu, A. D. Sezer, S. Bucak, Smart delivery systems with shape memory and self-folding polymers, Smart Drug Delivery System, InTech, (2016), p. 1-29.
K. Malachowski, M. Jamal, Q. Jin, B. Polat, C. J. Morris, D. H. Gracias, Self-folding single cell grippers. Nano Letters. 14, 4164-4170 (2014).
B. Gimi, T. Leong, Z. Gu, M. Yang, D. Artemov, Z. M. Bhujwalla, D. H. Gracias, Self-assembled three dimensional radio frequency (RF) shielded containers for cell encapsulation. Biomed. Microdevices. 7, 341-345 (2005).
G. Stoychev, N. Puretskiy, L. Ionov, Self-folding all-polymer thermoresponsive microcapsules. Soft Matter. 7, 3277-3279 (2011).
Y. Liu, J. Genzer, M. D. Dickey, "2D or not 2D": Shape-programming polymer sheets. Progress in Polymer Science. 52, 79-106 (2016).
L. Ionov, Soft microongami: self-folding polymer films. Soft Matter. 7, 6786-6791 (2011).
F. Caruso, H. Lichtenfeld, M. Giersig, H. Möhwald, Electrostatic self-assembly of silica nanoparticle—polyelectrolyte multilayers on polystyrene latex particles. J. Am. Chem. Soc. 120, 8523-8524 (1998).

(56) References Cited

OTHER PUBLICATIONS

W. Jiang, G. Wang, Y. He, X. Wang, Y. An, Y. Song, L. Jiang, Photo-switched wettability on an electrostatic self-assembly azobenzene monolayer. Chemical Communications, 3550-3552 (2005).

T. M. Cooper, A. L. Campbell, R. L. Crane, Formation of polypeptide-dye multilayers by electrostatic self-assembly technique. Langmuir. 11, 2713-2718 (1995).

K. Cai, Y. Hu, K. D. Jandt, Y. Wang, Surface modification of titanium thin film with chitosan via electrostatic self-assembly technique and its influence on osteoblast growth behavior. J. Mater. Sci. Mater. Med. 19, 499 (2008).

Y. Liu, J. K. Boyles, J. Genzer, M. D. Dickey, Self-folding of polymer sheets using local light absorption. Soft Matter. 8, 1764-1769 (2012).

N. Geraldi, F. F. Ouali, R. Monis, G. McHale, M. Newton, Capillary origami and superhydrophobic membrane surfaces. Appl. Phys. Lett. 102, 214104 (2013).

A. Azam, T. G. Leong, A. M. Zarafshar, D. H. Gracias, Compactness determines the success of cube and octahedron self-assembly. PloS One. 4, e4451 (2009).

D. J. Filipiak, A. Azam, T. G. Leong, D. H. Gracias, Hierarchical self-assembly of complex polyhedral microcontainers. J Micromech Microengineering. 19, 075012 (2009).

C. Dai, J. Cho, In situ monitored self-assembly of three-dimensional polyhedral nanostructures. Nano Letters. 16, 3655-3660 (2016).

G. Stoychev, L. Guiducci, S. Turcaud, J. W. Dunlop, L. Ionov, Hole-Programmed Superfast Multistep Folding of Hydrogel Bilayers. Advanced Functional Materials. 26, 7733-7739 (2016).

B. A. Kowalski, T. C. Guin, A. D. Auguste, N. P. Godman, T. J. White, Pixelated Polymers: Directed Self Assembly of Liquid Crystalline Polymer Networks. ACS Macro Lett. (2017) 6, 436-441.

J. Guan, H. He, D. J Hansford, L. J. Lee, Self-folding of three-dimensional hydrogel microstructures. The Journal of Physical Chemistry B. 109, 23134-23137 (2005).

D. Deng, Y. Chen, Origami-based self-folding structure design and fabrication using projection based stereolithography. Journal of Mechanical Design. 137, 021701 (2015).

M. Han, J. Hyun, E Sim, Self-rolled nanotubes with controlled hollow interiors by patterned grafts. Soft Matter. 11, 3714-3723 (2015).

T. S. Shim, Z. G. Estephan, Z. Qian, J. H. Prosser, S. Y. Lee, D. M. Chenoweth, D. Lee, S. J. Park, J. C. Crocker, Shape changing thin films powered by DNA hybridization. Nature Nanotechnology. 12, 41 (2017).

S. Zakharchenko, E. Sperling, L. Ionov, Fully biodegradable self-rolled polymer tubes: a candidate for tissue engineering scaffolds. Biomacromolecules. 12, 2211-2215 (2011).

V. Luchnikov, O. Sydorenko, M. Stamm, Self-Rolled Polymer and Composite Polymer/Metal Micro-and Nanotubes with Patterned Inner Walls. Adv Mater. 17, 1177-1182 (2005).

M. Jamal, A. M. Zarafshar, D. H. Gracias, Differentially photo-crosslinked polymers enable self-assembling microfluidics. Nature Communications. 2, 527 (2011).

Y. Mao, K. Yu, M. S. Isakov, J. Wu, M. L Dunn, H. J. Qi, Sequential self-folding structures by 3D printed digital shape memory polymers. Scientific Reports. 5, 13616 (2015).

M. T. Tolley, S. M. Felton, S. Miyashita, D. Aukes, D. Rus, R. J. Wood, Self-folding origami: shape memory composites activated by uniform heating. Smart Mater. Struct. 23, 094006 (2014).

C. Li, J. Adamcik, R. Mezzenga, Biodegradable nanocomposites of amyloid fibrils and graphene with shape-memory and enzyme-sensing properties. Nature Nanotechnology. 7, 421 (2012).

S. Janbaz, R. Hedayati, A. Zadpoor, Programming the shape-shifting of flat soft matter: from self-rolling/self-twisting materials to self-folding origami. Materials Horizons. 3, 536-547 (2016).

D. H. Gracias, V. Kavthekar, J. C. Love, K. E. Paul, G. M. Whitesides, Fabrication of micrometer-scale, patterned polyhedra by self-assembly. Adv Mater. 14, 235 (2002).

D. B. Burckel, S. Campione, P. S. Davids, M. B. Sinclair, Three dimensional metafilms with dual channel unit cells. Appl. Phys. Lett. 110, 143107 (2017).

D. Joung, T. Gu, J. Cho, Tunable Optical Transparency in Self-Assembled Three-Dimensional Polyhedral Graphene Oxide. ACS Nano. 10, 9586-9594 (2016).

T. G. Leong, P. A. Lester, T. L. Koh, E. K. Call, D. H. Gracias, Surface tension-driven self-folding polyhedra. Langmuir. 23, 8747-8751 (2007).

T. G. Leong, A. M. Zarafshar, D. H. Gracias, "Three-Dimensional Fabrication at Small Size Scales", Small. 2010, 6(7), 792-806.

J. Cho, M. D. Keung, N. Verellen, L. Lagae, V. V. Moshchalkov, P. Van Dorpe, D. H. Gracias, "Nanoscale origami for 3D optics", Small, 2011, 7(14), 1943-1948.

J. Cho, S. Hu, D. Gracias, "Self-assembly of orthogonal three-axis sensors", Appl. Phys. Lett. 2008, 93(4), 043505.

C. Chen, A. Ishikawa, Y. Tang, M. Shiao, D. P. Tsai, T. Tanaka, "Uniaxial-isotropic Metamaterials by Three-Dimensional Split-Ring Resonators", Adv. Optical Mater. 2015, 3(1), 44-48.

H. He, J. Guan, J. L. Lee, J., "An oral delivery device based on self-folding hydrogels", Journal of Controlled Release, 2006, 110(2), 339-346.

R. Fernandes, D. H. Gracias, "Self-folding polymeric containers for encapsulation and delivery of drugs", Adv. Drug Deliv. Rev. 2012, 64(14), 1579-1589.

C. L. Randall, T. G. Leong, N. Bassik, D. H. Gracias, "3D lithographically fabricated nanoliter containers for drug delivery", Adv. Drug Deliv. Rev. 2007, 59(15), 1547-1561.

V. Stroganov, S. Zakharchenko, E. Sperling, A. K. Meyer, O. G. Schmidt, L. Ionov, "Biodegradable Self-Folding polymer films with controlled Thermo-Triggered folding", Adv. Funct. Mater. 2014, 24(27), 4357-4363.

M. Jamal, N. Bassik, J. Cho, C. L. Randall, D. H. Gracias, "Directed growth of fibroblasts into three dimensional micropatterned geometries via self-assembling scaffolds", Biomaterials. 2010, 31(7), 1683-1690.

H. R. Kwag, J. V. Serbo, P. Korangath, S. Sukumar, L. H. Romer, D. H. Gracias, "A Self-Folding Hydrogel in Vitro Model for Ductal Carcinoma", Tissue Engineering Part C: Methods. 2016, 22(4), 398-407.

C. L. Randall, Y. V. Kalinin, M. Jamal, T. Manohar, D. H. Gracias, "Three-dimensional microwell arrays for cell culture", Lab on a Chip. 2011, 11(1), 127-131.

Y. V. Kalinin, J. S. Randhawa, D. H. Gracias, "Three-Dimensional Chemical Patterns for Cellular Self-Organization", Angew. Chem. Int. Edi. 2011, 50(11), 2549-2553.

B. Gimi, T. Leong, Z. Gu, M. Yang, D. Artemov, Z. M. Bhujwalla, D. H. Gracias, "Self-assembled three dimensional radio frequency (RF) shielded containers for cell encapsulation", Biomed. Microdevices. 2005, 7(4), 341-345.

K. Malachowski, M. Jamal, Q. Jin, B. Polat, C. J. Morris, D. H. Gracias, "Self-Folding Single Cell Grippers", Nano Lett. 2014, 14(7), 4164-4170.

A. Azam, K. E. Laflin, M. Jamal, R. Fernandes, D. H. Gracias, "Self-folding micropatterned polymeric containers", Biomed. Microdevices. 2011, 13(1), 51-58.

E. Iwase, I. Shimoyama, "Multistep Sequential Batch Assembly of Three-Dimensional Ferromagnetic Microstructures with Elastic Hinges", J Microelectromech Syst. 2005, 14(6), 1265-1271.

Y. W. Yi, C. Liu, "Magnetic Actuation of Hinged Microstructures", IEEE J Microelectromech Syst. 1999, 8(1), 10-17.

J. W. Judy, R. S. Muller, "Magnetically Actuated, Addressable Microstructures", J Microelectromech Syst. 1997, 6(3), 249-256.

S. J. Kim, H. I. Kim, S. J Park, I. Y. Kim, S. H. Lee, T. S. Lee, S. I. Kim, "Behavior in electric fields of smart hydrogels with potential application as bio-inspired actuators", Smart Mater Struct. 2005, 14(4), 511.

J. Guan, H. He, D. J. Hansford, L. J. Lee, "Self-Folding of Three-Dimensional Hydrogel Microstructures", The Journal of Physical Chemistry B. 2005, 109(49), 23134-23137.

M. Shahinpoor, Y. Bar-Cohen, J. Simpson, J. Smith, "Ionic polymer-metal composites (IPMCs) as biomimetic sensors, actuators and artificial muscles—a review", Smart Mater. Struct. 1998, 7(6), R15.

(56) References Cited

OTHER PUBLICATIONS

S. J. Kim, K. J. Lee, S. I. Kim, Y. M. Lee, T. D. Chung, S. H. Lee, "Electrochemical Behavior of an Interpenetrating Polymer Network Hydrogel Composed of Poly(proylene glycol) and Poly(acrylic acid)", J Appl Polym Sci. 2003, 89(9), 2301-2305.

C. Steinert, J. Mueller-Diekmann, M. Weiss, M. Roessle, R. Zengerle, P. Koltay, "Miniaturized and highly parallel protein crystallization on a microfluidic disc", presented at Micro Electro Mechanical Systems, 2007. MEMS. IEEE 20th International Conference on 2007.

Y. Lu, C. Kim, "Microhand for biological applications", Appl. Phys. Lett. 2006, 89(16), 164101.

M. Jamal, A. M. Zarafshar, D. H. Gracias, "Differentially photo-crosslinked polymers enable self-assembling microfluidics", Nat. Commun. 2011, 2, 527.

V. Luchnikov, O. Sydorenko, M. Stamm, "Self-Rolled Polymer and Composite Polymer/Metal Micro- and Nnanotubes with Patterned Inner Walls**", Adv Mater. 2005, 17(9), 1177-1182.

S. Zakharchenko, E. Sperling, L. Ionov, "Fully Biodegradable Self-Rolled Polymer Tubes: A Candidate for Tissue Engineering Scaffolds", Biomacromolecules. 2011, 12(6), 2211-2215.

T. S. Shim, S. Kim, C. Heo, H. C. Jeon, S. Yang, "Controlled Origami Folding of Hydrogel Bilayers with Sustained Reversibility for Robust Microcarriers**", Angew. Chem. Int. Ed. 2012, 51(6), 1420-1423.

V. Luchnikov, K. Kumar, M. Stamm, "Toroidal hollow-core microcavities produced by self-rolling of strained polymer bilayer films", J. Micromech. Microeng. 18 (2008), 1-5.

D. J. Filipiak, A. Azam, T. G. Leong, D. H. Gracias, "Hierarchical self-assembly of complex polyhedral microcontainers", J Micromech Microengineering. 2009, 19(7), 075012.

A. Azam, T. G. Leong, A. M. Zarafshar, D. H. Gracias, "Compactness Determines the Success of Cube and Octahedron Self-Assembly", PloS one. 2009, 4(2), e4451.

C. Dai, J. H. Cho, "In Situ Monitored Self-Assembly of Three-Dimensional Polyhedral Nanostructures", Nano Lett., 2016, 16 (6), 3655-3660.

T. G. Leong, P. A. Lester, T. L. Koh, E. K. Call, D. H. Gracias, "Surface Tension-Driven Self-Folding Polyhedra", Langmuir. 2007, 23(17), 8747-8751.

S. Janbaz, R. Hedayati, A. Zadpoor, "Programming the shape-shifting of flat soft matter: from self-rolling/self-twisting materials to self-folding origami†", Materials Horizons. 2016, 3(6), 536-547.

D. H. Gracias, V. Kavthekar, J. C. Love, K. E. Paul, G. M. Whitesides, "Fabrication of Micrometer-Scale, Patterned Polyhedra by Self-Assembly**", Adv Mater. 2002, 14(3), 235.

D. Joung, K. Agarwal, H. Park, C. Liu, S. Oh, J. Cho, "Self-Assembled Multifunctional 3D Microdevices", Adv. Elect. Mater. 2016, 2(6), 1500459.

D. Joung, T. Gu, J. Cho, "Tunable Optical Transparency in Self-Assembled Three-Dimensional Polyhedral Graphene Oxide", ACS nano. 2016, 10(10), 9586-9594.

J. C. Breger, C. Yoon, R. Xiao, H. R. Kwag, M. O. Wang, J. P. Fisher, T. D. Nguyen, D. H. Gracias, "Self-Folding Thermo-Magnetically Responsive Soft Microgrippers", ACS applied materials & interfaces. 2015, 7(5), 3398-3405.

E. Gultepe, J. S. Randhawa, S. Kadam, S. Yamanaka, F. M. Selaru, E J. Shin, A. N. Kalloo, D. H. Gracias, "Biopsy with Thermally-Responsive Untethered Microtools", Adv. Mater. 2013, 25(4), 514-519.

D. Davis, R. Mailen, J. Genzer, M. D. Dickey, "Self-folding of polymer sheets using microwaves and graphene ink†", RSC Advances. 2015, 5(108), 89254-89261.

D. G. Fink, A. A. McKenzie, New York: McGraw-Hill, 1975, edited by Fink, Donald G.; McKenzie, Alexander A., "Molecular Methods in Plant Pathology", 1975.

H. Crew, General physics: an elementary text-book for colleges, Electric Currents, Macmillan 1908, pp. 409-412.

M. N. Sadiku, Elements of electromagnetics, Oxford University Press 2014, p. 375.

R. F. Harrington, Introduction to electromagnetic engineering, Courier Corporation 2003, p. 1-7.

F. Fiorillo, Characterization and measurement of magnetic materials, Academic Press 2004, p. 1-7.

D. Halliday, J. Walker, R. Resnick, Fundamentals of Physics, Chapter 30, John Wiley & Sons 2010, pp. 864-869.

H. Janocha, "Microactuators-principles, applications, trends", presented at Proc. MICRO. tec 2000, VDE World Microtechnology Congress 2000, p. 1-8.

* cited by examiner

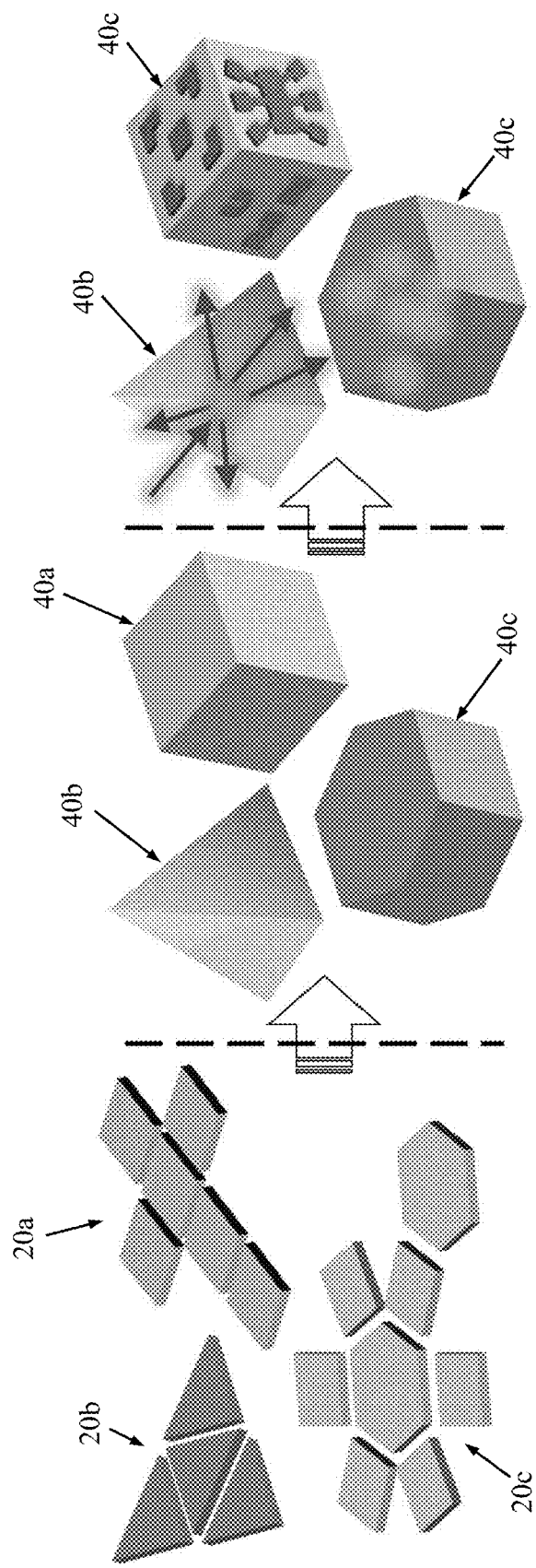

METHOD OF MANUFACTURING A REMOTE-CONTROLLED MICRO-SCALE THREE-DIMENSIONAL SELF-ASSEMBLY

CROSS-REFERENCE TO RELATED APPLICATIONS

This Non-Provisional Patent Application claims the benefit of the filing date of U.S. Provisional Patent Application Ser. No. 62/514,205, filed Jun. 2, 2017, the entire teachings of which are incorporated herein by reference.

STATEMENT REGARDING FEDERALLY SPONSORED RESEARCH OR DEVELOPMENT

This invention was made with government support under CMMI 1454293 awarded by the National Science Foundation. The government has certain rights in this invention.

BACKGROUND

The present disclosure relates to three-dimensional (3D) micro-scale structures. More particularly, it relates to methods of making 3D micro-scale structures.

Three-dimensional (3D) micro/nanostructures with various shapes, architectures, and materials have recently been the subject of increased attention, because their dimensionality strongly influences their physical and chemical responses to surrounding environmental media as compared to two-dimensional (2D) micro/nanostructures. Conventional 3D fabrications are typically built using layer-by-layer (LBL) lithographic patterning methods, 3D printing, and/or self-aligned membrane projection lithography. More recently, origami-like, self-folding or self-assembly techniques have been developed.

Self-folding is a deterministic self-assembly process, providing a desirable strategy for creating three-dimensional (3D) micro-scale structures for 3D sensing, 3D metamaterials, drug delivery, cell cultures, cell encapsulation and micro-scale chemical container applications. In general terms, self-folding assembly entails the initial formation of a two-dimensional (2D) net of micro-scale panels connected to one another by a hinge material. The physical or chemical property of the hinge materials is caused to change, generating a surface tension force that causes the panels of the 2D net to self-fold relative to one another, resulting in a 3D micro-scale structure. In order to trigger or generate the physical or chemical property changes, external heat energy has been mainly used. For example, for thermal sensitive hinges, the phase transition (from solid to liquid) occurs when the hinge material absorbs heat energy, which generates surface tension forces for self-assembly. The heat energy is usually applied from an external source, such as a hotplate or a hot liquid bath, which requires direct contact between the heat source and the hinge materials. Another way to induce changes in the physical/chemical property is to apply environmental (e.g., pH or ionic strength) changes to solvent-sensitive hinge materials. Physical/chemical reactions occur when solvents are in contact with the hinge materials, triggering the self-assembly.

While viable, a drawback of conventional self-assembly processes is that the direct contact of heat energy sources or chemicals with the hinge materials critically limits its applications and reduces the manipulative capability of the self-assembly because the heat sources are not controllable and the environment around the microstructures is not accessible in many practical situations. For example, with many contemplated biomedical end use application, it is desirable to initiate the self-assembly process in a 2D net located within the human body (e.g., microrobots for surgery and tissue sampling, drug delivery); with these and other end use applications, direct contact heat source or chemical is not suitable. Moreover, direct heat energy sources, such as a hotplate or a hot liquid bath, usually have a high thermal mass, leading to a thermal lag (or time delay) from when the input energy is controlled to when the 2D net begin to self-fold or assemble. Thus, the assembling process cannot be precisely controlled using such methods.

SUMMARY

The inventors of the present disclosure recognized that a need exists for 3D micro-scale structures and methods of making the same that overcome one or more of the above-mentioned problems.

Some aspects of the present disclosure relate to methods of manufacturing a 3D micro-scale structure. The method includes providing a 2D net. The 2D net includes a plurality of panels and a plurality of hinges. The panels (e.g., micro-scale panels) arranged in a pattern or array conducive to folding into a 3D shape. Each of the hinges interconnect immediately adjacent ones of the panels within the pattern. An energy source remote from the 2D net is powered to deliver energy to the 2D net. The delivered energy triggers the 2D net to self-fold into a 3D micro-scale structure. In this regard, the delivered energy creates an eddy current within at least one component of the 2D net, with the eddy current generating heat sufficient to melt the hinges. The melting hinges cause the corresponding panels associated with the melting hinges to fold or pivot relative to one another. In some embodiments, the energy source is a microwave energy source. In other embodiments, the energy source operates to deliver a magnetic field to the 2D net.

In some non-limiting embodiments, the 2D net incorporates at least one thin metal film (e.g., chromium) and polymeric hinges. The thin metal film absorbs electromagnetic microwaves and generates heat energy to induce reflow of the polymeric hinges, leading to self-assembly of 3D micro-scale structure. Since this assembly process does not require direct contact with a heat source or chemicals, micro-scale actuations can be achieved in a remote location without physical contact, resulting in the powerful capability to manipulate the 3D assembly process in situations where the heat sources and the environment around the microstructures are not controllable and accessible. Multiple folding configurations of the microstructures can also be achieved simultaneously with a single microwave energy source by forming different metal film thicknesses adjacent to the polymer hinges. Thus, remote-controlled self-assembly using microwave energy might be applied for the development of 3D micro-scale-sensors, micro-scale-microbots, and micro-scale-metamaterials.

In other non-limiting embodiments, the panels of the 2D include a metal (e.g., nickel), and the hinges are formed of a polymer with a relatively low melting point. A rapid changing magnetic field provided by an induction coil generates eddy current inside the panels, with heat dissipation of the eddy current being great enough to melt the polymeric hinges that in turn generate a surface tension force sufficient to articulate or fold the metallic panels relative to one another. The induction heating is localized to the metal panels, and is minimal, if any, effect on the surrounding environment. The induction magnetic field can penetrate through biomaterials. Induction heating can trigger self-assembly without harming live organs or tissues, and can be useful, for example, with biomedical applications such as cell encapsulation, cell culture, biomedical sensing, and drug delivery.

BRIEF DESCRIPTION OF THE DRAWINGS

FIGS. 2A-2C schematically illustrate differently shaped 2D nets and 3D sensors in accordance with principles of the present disclosure;

DETAILED DESCRIPTION

Figure 1A:
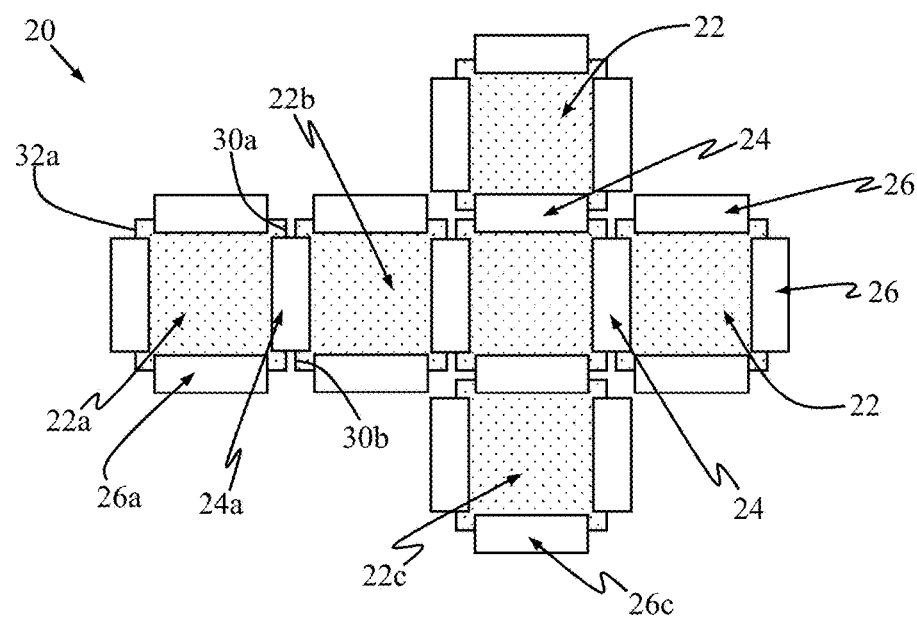
FIG. 1A is a simplified top plan view of a 2D net useful in forming 3D micro-scale structures in accordance with principles of the present disclosure.

Aspects of the present disclosure are directed toward 3D micro-scale structures and methods of making the same, and in particular self-folding manufacturing techniques triggered by an indirect energy source. In general terms, the self-folding process is akin to origami in which a 2D micro-scale structure or net self-folds into a 3D micro-scale structure. For example, FIG. 1A illustrates a 2D net 20 from which a 3D micro-scale structure (e.g., polyhedral shape such as a cube) of the present disclosure can be generated. The 2D net 20 includes a plurality of micro-scale panels 22, hinges 24, and optional joint structures 26. Each of the panels 22 can be a continuous or homogenous body. In other embodiments, each of the panels 22 can include an outer frame forming a window in which a membrane is disposed (and is supported by the outer frame) as described, for example, in U.S. Patent Application Publication Nos. 2017/0294698 and 2017/0291819, the entire teachings of each of which is incorporated herein by reference. Optionally, one or more of the panels 22 can be functionalized (e.g., a metal pattern, biomaterial, etc., is applied to a face of the panel 22). In general terms, the primary structural component of each the panels 22 (e.g., an entirety of the panel 22 where the panel is a continuous or homogenous body, the outer frame with construction in which the panel 22 includes an outer frame supporting an inner membrane, etc.) can be formed of various materials, such as polymer (e.g., epoxy, photoresist, etc.), metal (e.g., nickel), insulators (e.g., $Al_2O_3$), etc. Respective ones of the hinges 24 extend between and interconnect opposing edges of immediately adjacent ones of the panels 22 in the array of the 2D net 20. A material of each of the hinges 24 is selected to exhibit desired properties when subjected to an environmental changes, such as in the presence of heat, and in some embodiments is a polymer (e.g., photoresist), solder (Pb—Sn), etc. Optionally, a transition body can be provided with the 2D net 20 that generates heat when energized as described below. Regardless, some methods of the present disclosure entail triggering the hinges 24 via an indirect energy source as described in greater detail below.

As initially provided in the form of the 2D net 20, the panels 22 are arranged in an array conducive to folding into a 3D polyhedral shape, with facing edges of immediately adjacent ones of the panels 22 being connected to one another by a corresponding one of the hinges 24. Stated otherwise, in the 2D net array, various panels 22 are arranged side-by-side or edge-to-edge; one of the hinges 24 extends between and interconnects the corresponding edges thereof. For example, first and second panels 22a, 22b are identified in FIG. 1A. In the array, the first panel 22a is immediately adjacent the second panel 22b, with a first edge 30a (referenced generally) of the first panel 22a facing or immediately proximate a first edge 30b of the second panel 22b. The first and second panels 22a, 22b are interconnected by a hinge 24a that extends between the first edges 30a, 30b. Other panel edges in the array of the 2D net 20 are free or not otherwise directly connected to another panel by a hinge. For example, a second edge 32a of the first panel 22a identified in FIG. 1A is not directly connected to a separate panel in the 2D net 20 state. In some embodiments, a joint structure 26 is provided at one or more (including all) of the panel free edges. Where provided, the joint structure 26 projects beyond the face of the corresponding panel 22 (e.g., FIG. 1A identifies joint structure 26a that is applied to the first panel 22a at the second edge 32a). A material of each of the joint structures 26 can be identical to that of the hinges 24 (e.g., polymer) for reasons made clear below.

Figure 1B:
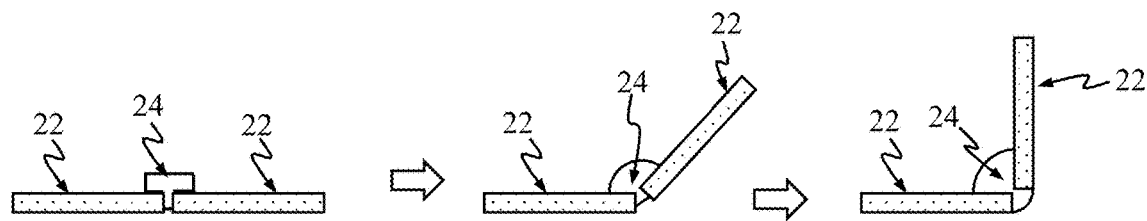
FIG. 1B schematically illustrates portions of methods of the present disclosure.
Figure 1C:
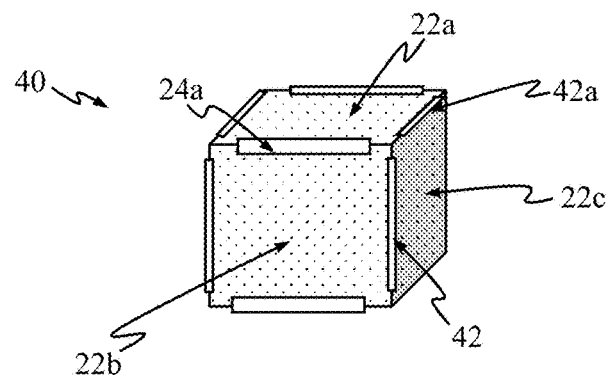
FIG. 1C is a simplified perspective view of a 3D micro-scale structure resulting from the 2D net of FIG. 1A.

In some embodiments, the 2D net 20 is configured such that when the 2D net 20 is subjected to energy from an indirect energy source, a temperature of the hinges 24 is raised to a critical point (e.g., melting point); the molten hinges 24 generate a surface tension force and cause the panels 22 to self-fold up into a 3D micro-scale structure (e.g., as a result of the polymer hinge melting (or reflow), a surface tension force is generated). For example, FIG. 1B schematically depicts self-folding of the hinge 24 and two of the panels 22 when the hinge 24 is subjected to heat. FIG. 1C illustrates a 3D micro-scale structure 40 resulting from origami-like self-folding of the 2D net 20. As a point of reference, and with additional reference to FIG. 1A, where provided, various ones of the joint structures 26 are brought into contact with one another and fuse upon self-folding of the 2D net 20, resulting in a completed joint 42 at a corresponding edge of the 3D micro-scale structure 40. For example, the first joint structure 26a is identified with the first panel 22a in FIG. 1A, as is a first joint structure 26c provided with a third panel 22c. The first-third panels 22a-22c are again labeled in FIG. 1C, along with the hinge 24a. With cross-reference between FIGS. 1A and 1C, one completed joint 42a of the 3D micro-scale structure 40 is generated by the first joint structure 26a of the first panel 22a and the first joint structure 26c of the third panel 22c upon completion of the self-folding operation.

The 2D net and resultant 3D micro-scale structures of the present disclosure can assume a wide variety of other shapes, such as any polyhedral shape, and are not limited to the cubic shape of FIG. 1C. For example, FIGS. 2A and 2B schematically illustrate conversion of 2D nets 20a, 20b, 20c into 3D micro-scale structures 40a, 40b, 40c of various 3D shapes. FIG. 2C schematically illustrates that the 3D micro-scale structures 40a, 40b, 40c of the present disclosure can be functionalized by surface patterning and/or encapsulating various materials (e.g., chemicals, biomaterials, etc.). Further, while in some embodiments, the 3D micro-scale structures of the present disclosure have a closed shape (e.g., the hollow, six sided cubic shape of the 3D micro-scale structure 40 in FIG. 1C), in other embodiments an open shape can be provided.

Against the above background and returning to FIG. 1A, methods of the present disclosure for triggering the self-folding process via an indirect energy source, along with optional 2D net and resultant 3D micro-scale structure constructions conducive to the methods, are described below.

Microwave Energy Source

Some methods of the present disclosure use remote-controlled microwave energy with the ability to control the self-assembly process on a micro-scale. This process can also allow for the control of multiple folding angles of the panels 22 relative to one another simultaneously, even when using a single energy source for self-assembly, by adjusting the various thicknesses of the hinges 24, with each thickness responding differently to the microwave. The folding angles of each the panel of the panels 22 relative to one another in the resultant 3D micro-scale structure 40 are precisely controlled by tuning the power of the microwave sources in a remote location, resulting in a powerful manipulative capability of the 3D assembly process in situations where the heat sources and the environment around the microstructures are not controllable and accessible.

Figure 3:
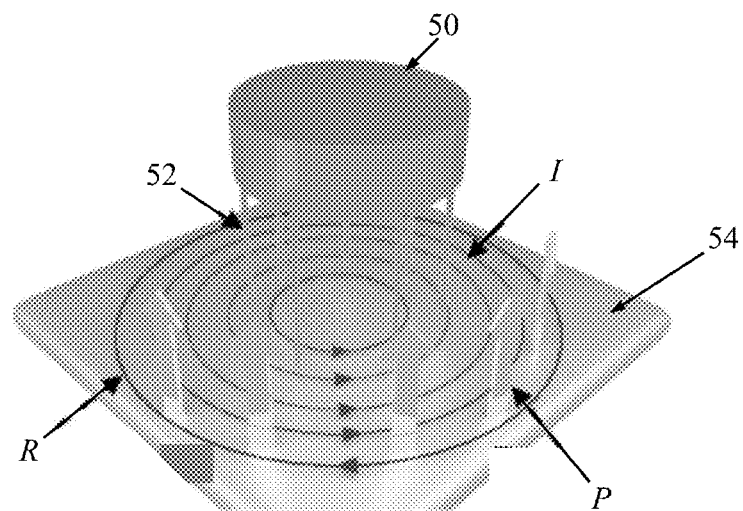
FIG. 3 schematically illustrates heat power generation within a thin film and useful with some methods of the present disclosure.

The microwave energy-based methods of the present disclosure are, in some embodiments, driven by Joule heating generated by eddy current within a transition body (e.g., thin metal film) provided with one or more or all of the hinges 24 and/or the joint structures 26. As a point of reference, FIG. 3 illustrates a microwave energy source 50 (e.g., a magnetron) emitting microwave energy 52 (e.g., electromagnetic waves) onto a thin metal film 54 (e.g., chromium (Cr)). The rapid-alternating electric and magnetic fields generated by the energy source 50 hit the thin metal film 54, and the magnetic field (B) induces a loop of electric current (I), namely eddy current, in the thin metal film 54 due to the changing magnetic field (B). The generated eddy current circulates in the thin metal film 54 and flows against the resistance (R) of the thin metal film 54. The electrical energy generated by the eddy current (I) in the thin metal film 54 is converted to thermal energy (P) through resistive loss due to Joule heating, the collision and friction of the electrons and conductors inside the thin metal film 54.

Figure 4:
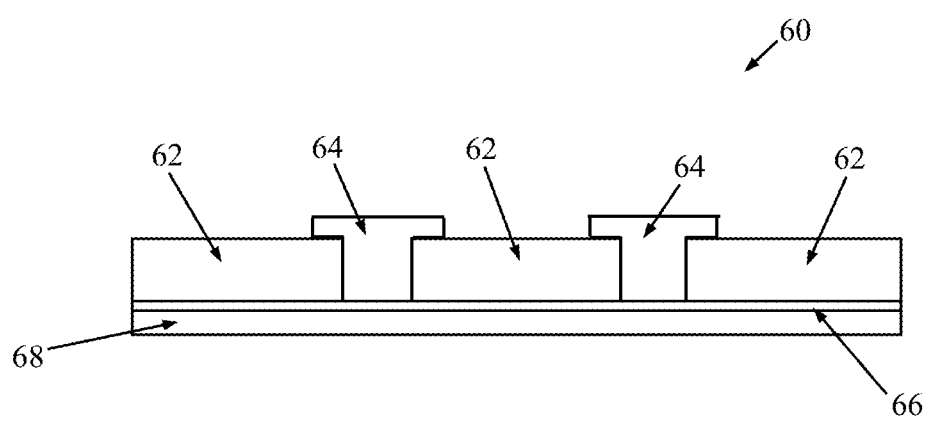
FIG. 4 is a simplified side view of a portion of a 2D net useful with methods of the present disclosure.

With the above in mind, a portion of a 2D net 60 in accordance with principles of the present disclosure is schematically shown in FIG. 4. The 2D net 60 is akin to the 2D net 20 (FIG. 1A) described above, and is generally configured for self-assembly to a 3D micro-scale structure using methods of the present disclosure. The 2D net 60 includes a plurality of micro-scale panels 62, a plurality of hinges 64, a transition body 66, and an optional support layer 68. In some non-limiting embodiments, each of the panels 62 is a continuous, homogenous body formed of a rigid material, such as an epoxy material (e.g., photodefinable epoxy available from MicroChem Corp. of Newton, Mass. under the trade designation SU-8), having a melting point higher than a melting point of a material of the hinges 64. In other embodiments, each of the panels 62 can have a multi-component configuration, such as an outer frame maintaining an inner membrane (that in turn can support other components, such as functionalized electronics) as described above. With these optional constructions, the individual components can be formed of differing materials; however, the selected materials each have a melting point higher than a melting point of a material of the hinges 64. Respective ones of the hinges 64 interconnect immediately adjacent panels 62. A shape of each of the hinges 64 is selected to generate a pivoting or folding motion or force onto the immediately adjacent panels 62 when heated to a melting point. In some embodiments, the hinges 64 are each formed of a polymer material with a melting point below a melting point of the panel frames, such as a polymer-based photoresist film available from MicroChem Corp. of Newton, Mass. under the trade designation Megaposit™ SPR™ 220, polycaprolactone (PCL), etc. The transition body 66 is a thin metal film (e.g., Cr), and is formed in close proximity to the hinges 64. In some embodiments, the transition body 66 has a size and shape that mimics a pattern of the panels 62. Regardless, in some embodiments, the transition body 66 contacts each of the hinges 64. Where provided, the support layer 68 can be formed of the same material as the panels 62, with the support layer 68 and the panels 62 encapsulating the transition body 66.

Figure 5A:
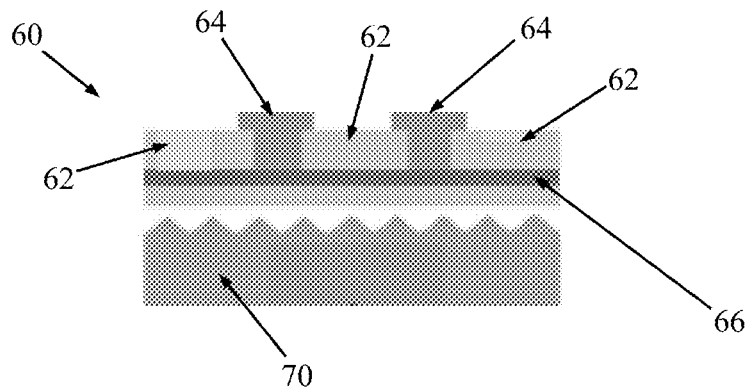
FIGS. 5A-5C schematically illustrate self-assembly of the 2D net of FIG. 4 into a 3D micro-scale structure in accordance with principles of the present disclosure.
Figure 5B:
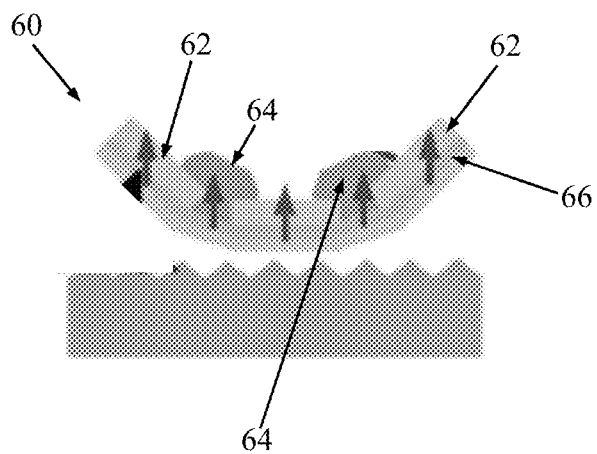
Figure 5C:
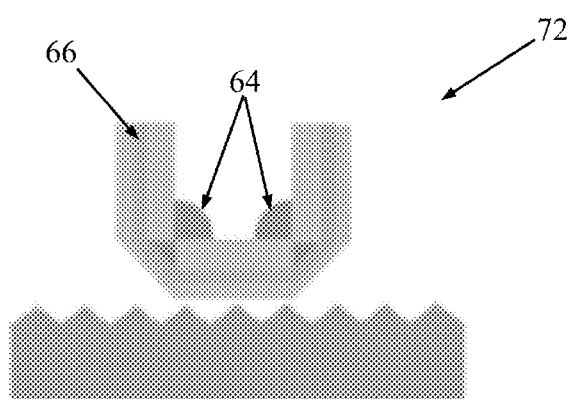

With some methods of the present disclosure, the 2D net 60 is triggered to self-assemble to a 3D micro-scale structure by subjecting the 2D net 60 to microwave energy. For example, in FIG. 5A, the 2D net 60 has been released from or formed on a substrate 70 (e.g., glass, paper, etc.). When remote-controlled microwave energy is applied to the 2D net 60, heat is generated within the transition body 66 due to the eddy current effect described above. The heat generated exceeds the melting point of the hinges 64. The melting hinges 64 generate surface tension forces towards the center of the hinges 64 as reflected by FIG. 5B. Since the panels 62 are rigid, the generated stress in the hinges 64 can lift up the panels 62, hence realizing the self-assembly of the 2D net 60 into a 3D micro-scale structure 72 as in FIG. 5C. After the microwave energy source is shut down, the temperature of the 3D micro-scale structure 72 can rapidly decrease to room temperature due to the low mass and large surface areas of the transition body 66. The molten hinges 64 re-solidify to their original phase and the shape of the self-folded structure 72 is maintained.

Figure 6:
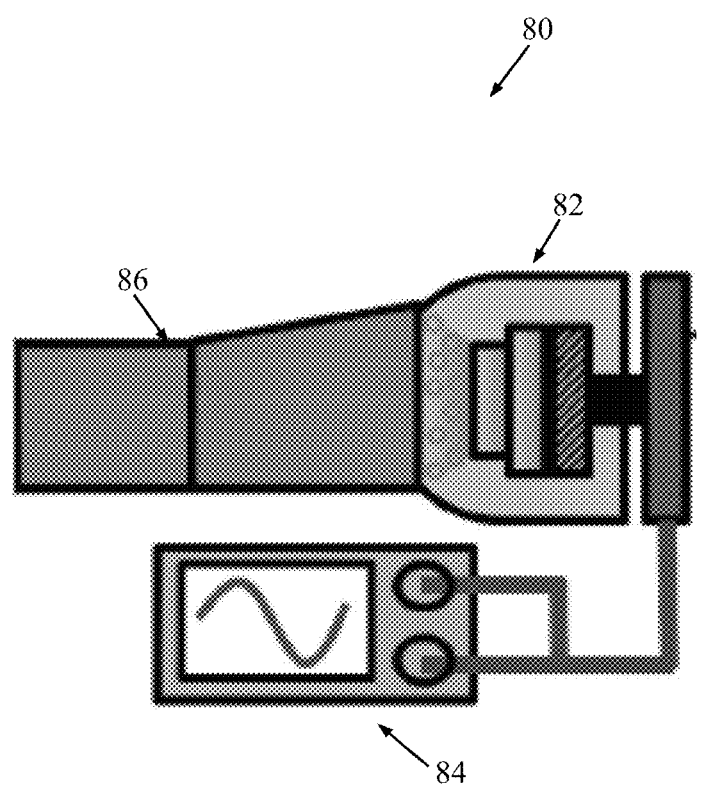
FIG. 6 is a simplified view of an energy source useful with methods of the present disclosure.

One example of a microwave energy source 80 useful with some methods of the present disclosure is shown in FIG. 6. The energy source 80 includes a microwave generator 82, a power supply 84 and a waveguide 86. The microwave generator 82 and power supply 84 can assume various forms as known in the art, for example capable of operating at a frequency in the range of 0.5-5 GHz. In one illustrative example, a commercialized 1050-watt magnetron (model number M24FA-410A available from Guangdong Galanz Enterprise Co, ltd., Guangdong Province, China) can be used as the microwave generator 82, and methods of the present disclosure can be performed with the microwave generator 82 operating at a frequency of 2.45 GHz. Other frequencies are also acceptable. The waveguide 84 is optically associated with an emitting end of the microwave generator 82, and is configured to direct emitted waves toward the 2D net to be energized. Regardless, with some methods of the present disclosure, since the energy is remotely transmitted to the 2D net by electromagnetic radiation, no direct contact between the stimuli source (the microwave energy source 80) and the 2D net is required. The remotely transmitted electromagnetic radiation generates heat energy, leading to reflow in hinge materials of the 2D net for self-assembly as described above.

Figure 7A:
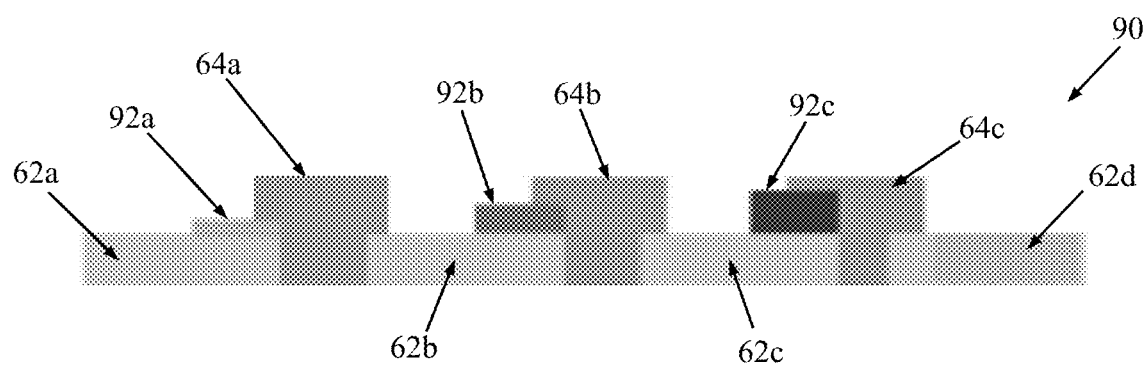
FIG. 7A is a simplified side view of a portion of a 2D net useful with methods of the present disclosure.

Returning to FIG. 4, while the transition body 66 has been shown as having a size and shape commensurate with the pattern of the panels 62, other constructions are also acceptable. For example, a footprint or size of the transition body 66 can be less than that of the pattern of the panels 62. In other embodiments, two or more of the transition bodies can be provided. For example, FIG. 7A illustrates portions of another 2D net 90 in accordance with principles of the present disclosure is schematically shown in FIG. 4. The 2D net 90 is akin to the 2D net 60 (FIG. 4) described above, and is generally configured for self-assembly to a 3D micro-scale structure using, for example, the microwave energy source methods of the present disclosure. The 2D net 90 includes the plurality of micro-scale panels (identified at 62a, 62b, 62c, 62d) and the plurality of hinges (identified at 64a, 64b, 64c in FIG. 7A) as described above, and a plurality of transition bodies, such as transition bodies 92a, 92b, 92c. As described above, each of the panels 62a-62d can be a continuous, homogenous body, or can include an outer frame supporting an inner membrane. Materials of the panels 62a-62d, hinges 64a-64c and transition bodies 92a-92c can have any of the forms described above.

Figure 7B:
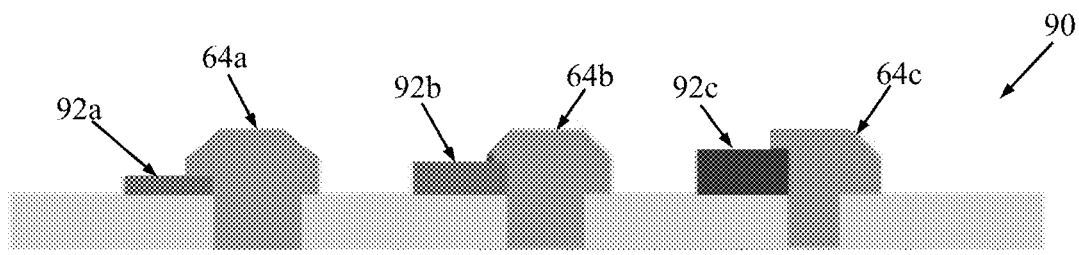
FIGS. 7B and 7C schematically illustrate self-assembly of the 2D net of FIG. 7A into a 3D micro-scale structure in accordance with principles of the present disclosure.
Figure 7C:
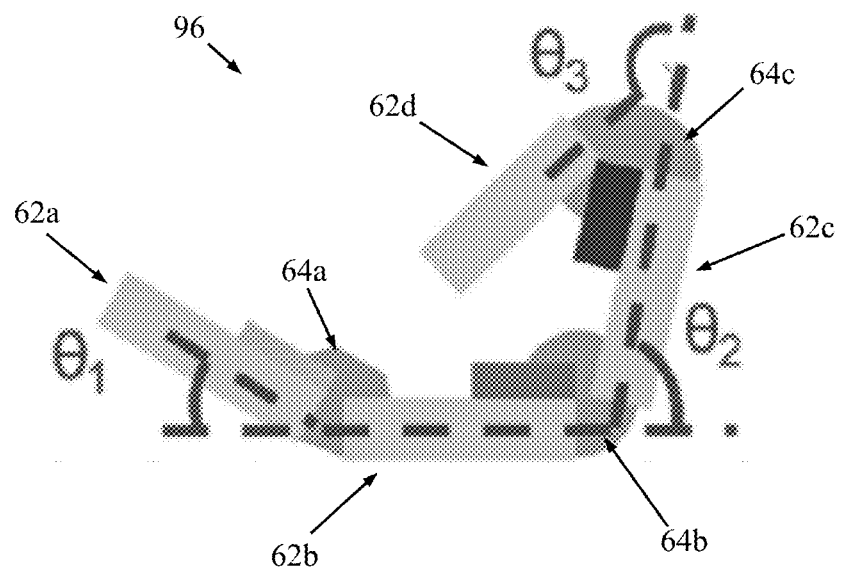

With the embodiment of FIG. 7A, each of the transition bodies 92a-92c are relatively small (as compared to a footprint or size of the pattern of panels 62a-62d), and respective ones of the transition bodies 92a-92c are disposed immediately adjacent (e.g., directly contacting) a corresponding one of the hinges 64a-64c. In some embodiments, the transition bodies 92a-92c can be identical in terms of size and shape. In other embodiments, such as with the 2D net 90, one or more of the transition bodies 92a-92c can have a differing dimension, such as thickness, with this differing dimension generating a unique folding angle between the panels 62a-62d of the corresponding hinge 64a-64c. For example, with the non-limiting construction of FIG. 7A, a thickness of the first transition body 92a is less than a thickness of the second transition body 92b, and the thickness of the second transition body 92b is less that a thickness of the third transition body 92c. As a result, and as generally reflected by FIG. 7B, when the 2D net 90 is subjected to microwave energy as described above, different amount of heat are generated by the transition bodies 92a-92c as a function of thickness. Thus, the first hinge 64a is heated to a lesser extent than the second hinge 64b, and the second hinge 64b is heated to a lesser extent than the third hinge 64c. As a result, and as shown in the resultant 3D micro-scale structure 96 of FIG. 7C, a folding angle $\theta_1$ between the first and second panels 62a, 62b as effected by the first hinge 64a is less than a folding angle $\theta_2$ between the second and third panels 62b, 62c as effected by the second hinge 64b, etc.

Magnetic Field Energy Source

Some methods of the present disclosure use a remote-controlled magnetic field energy source (electromagnetic waves), with the magnetic field producing localized heating as described below. The magnetic field can be biocompatible and safe to use around living tissues and organs, for example under circumstances where microwave energy may be harmful. The methods can be beneficial in situations where the heat sources and the environment around the microstructures are not controllable and accessible.

With reference to FIG. 1A, the magnetic field energy-based methods of the present disclosure are, in some embodiments, useful with 2D net 20 constructions in which the panels 22 (or a primary structural component thereof, such as an outer frame) are formed of a metal material (e.g., nickel), and are driven by Joule heating generated by eddy current within the panels 22. The localized heat increases the surface temperature of the 2D net sufficient to melt the hinges 24 (that can be formed of a material having a low melting point, such as PCL in some non-limiting embodiments). The magnetic field energy source or induction system can assume various forms known in the art, and generally includes an induction coil. In some embodiments, the magnetic field energy source is capable of generating a high frequency magnetic field, for example on the order of 1-10 MHz. In one non-limiting example, the induction induced magnetic field operates at a frequency of 5 MHz, which is high enough to generate heat to trigger the self-assembly process, but low enough not to harm human bodies, living tissues and organs. In some embodiments, the magnetic field energy source can be a conventional magnetic resonance imaging (MM) scanner commonly used with human medical imaging.

Figure 8:
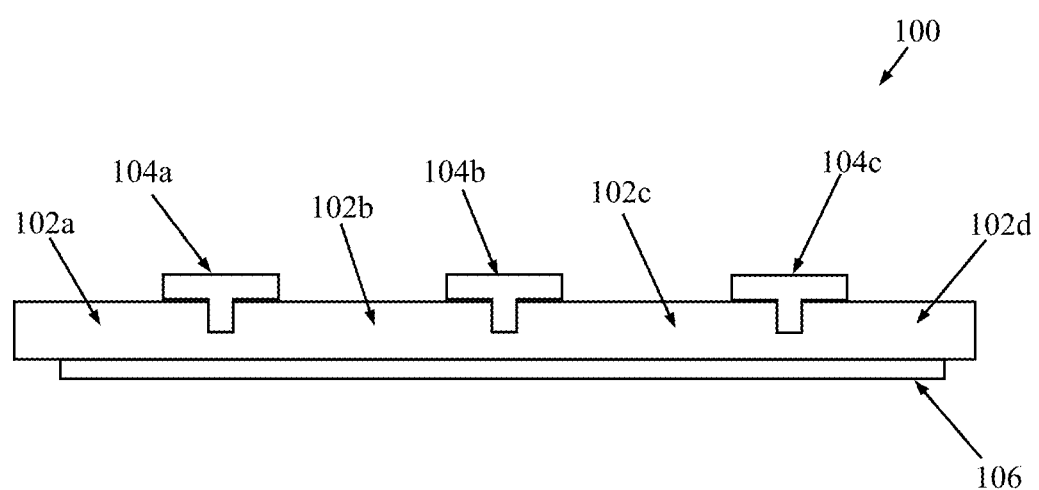
FIG. 8 is a simplified side view of a portion of a 2D net useful with methods of the present disclosure FIG. 6.

With the above in mind, a portion of a 2D net 100 in accordance with principles of the present disclosure and useful with the magnetic field energy source or induction source methods of the present disclosure is schematically shown in FIG. 8. The 2D net 100 is akin to the 2D net 20 (FIG. 1A) described above, and is generally configured for self-assembly to a 3D micro-scale structure using methods of the present disclosure. The 2D net 100 includes a plurality of micro-scale panels (such as panels 102a, 102b, 102c, 102d), a plurality of hinges (such as hinges 104a, 104b, 104c), and a supporting layer 106. In some non-limiting embodiments, each of the panels 102a-102d is a continuous, homogenous body formed of a metal material, such as nickel. In other embodiments, each of the panels 102a-102d can have a multi-component configuration, such as an outer frame maintaining an inner membrane (that in turn can support other components, such as functionalized electronics) as described above. With these optional constructions, the individual components can be formed of differing materials; however, at least one structural component (e.g., an outer frame) is formed of a metal material such as nickel.

The supporting layer 106 maintains the panels 102a-102d relative to one another, and in some embodiments can be considered a portion of each of the panels 102a-102d (e.g., the membrane 28 (FIG. 1A) described above). Respective ones of the hinges 104a-104c interconnect immediately adjacent panels 102a-102d. A shape of each of the hinges 104a-104c is selected to generate a pivoting or folding motion or force onto the immediately adjacent panels 102a-102d when heated to a melting point. In some embodiments, the hinges 104a-104c are each formed of a polymer material with a melting point below a melting point of the panels 102a-102d, such as polycaprolactone (PCL), a polymer-based photoresist film available from MicroChem Corp. of Newton, Mass. under the trade designation SPR 220, etc. The supporting layer 106 can be a thin metal film (e.g., $Al_2O_3$), and is formed along the panels 102a-102d opposite the hinges 104a-104c.

Figure 9A:
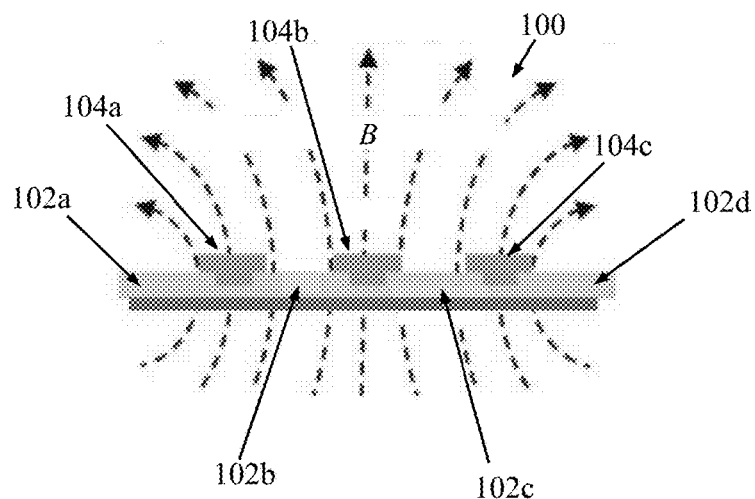
FIGS. 9A-9C schematically illustrate self-assembly of the 2D net of FIG. 8 into a 3D micro-scale structure in accordance with principles of the present disclosure.
Figure 9B:
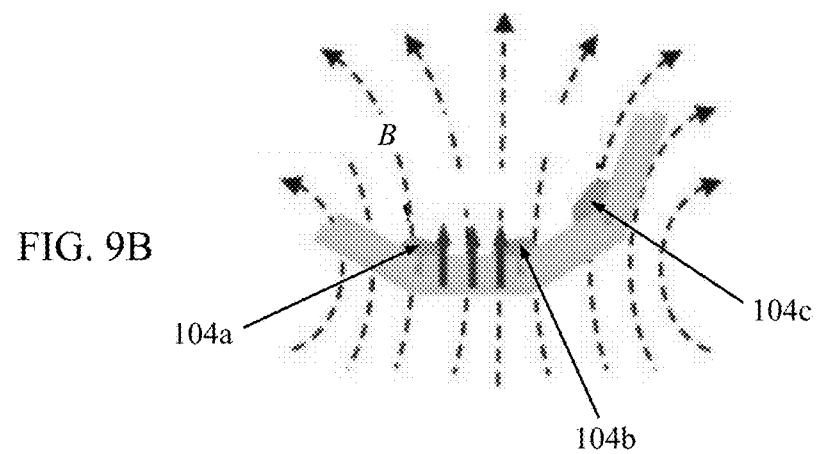
Figure 9C:
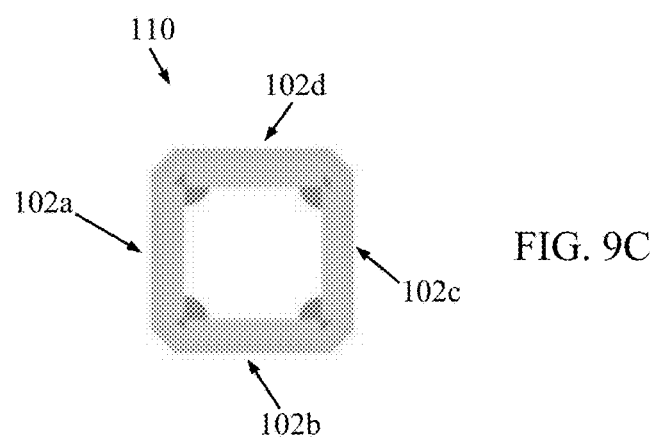
Figure 10A:
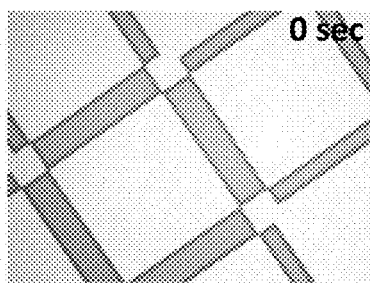
FIGS. 10A-10H are optical images of hinge reflow as described in the Examples section.
Figure 10B:
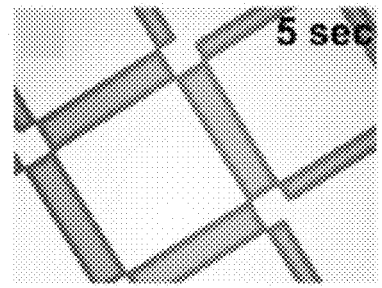
Figure 10C:
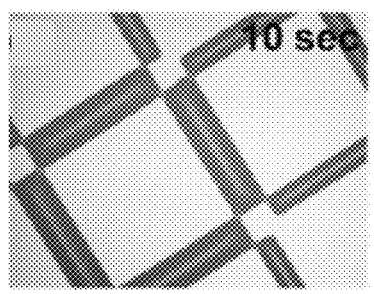
Figure 10D:
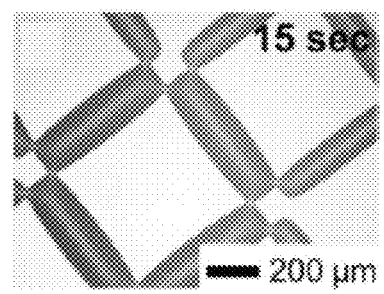
Figure 10E:
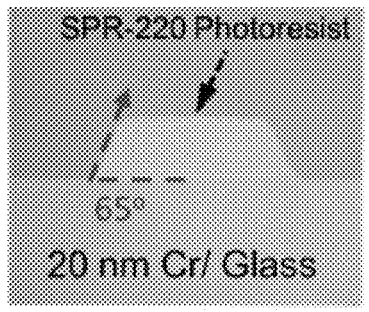
Figure 10F:
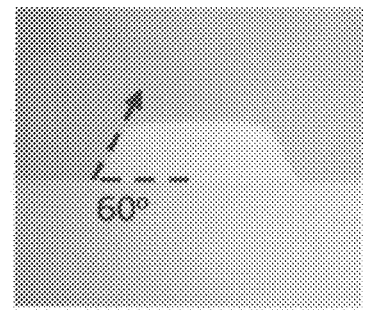
Figure 10G:
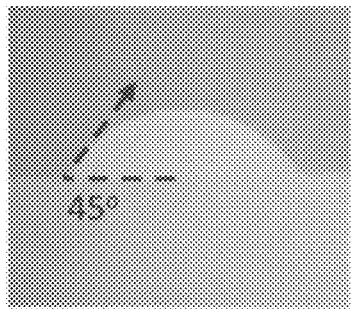
Figure 10H:
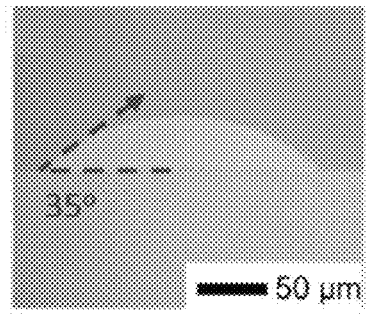

As shown in FIG. 9A, with some methods of the present disclosure, an induction coil (not shown) or other magnetic field energy source is operated to subject the 2D net 100 to a magnetic field (B) (referenced generally). The magnetic field B induces a loop of electric current (I), namely eddy current, in metal material of the panels 102a-102d due to the time-varying or changing magnetic field B. The generated eddy current circulates in the respective panels 102a-102d (e.g., the eddy current forms a current closed loop in places that are perpendicular to the magnetic field inside the corresponding panel 102a-102d) and flows against the resistance (R) of the metal material of the panel 102a-102d, which dissipates energy as heat due to Joule's law. The heat energy is transferred to the hinges 104a-104c sufficient to cause the hinges 104a-104c to melt (i.e., the heat generated exceeds the melting point of the hinges 104a-104c). The melting hinges 104a-104c generate surface tension forces towards the center of the hinges 104a-104c as reflected by FIG. 9B. Since the panels 102a-102d are rigid, the generated stress in the hinges 104a-104c can lift up the panels 102a-102d, hence realizing the self-assembly of the 2D net 100 into a 3D micro-scale structure 110 as in FIG. 9C. After the magnetic field energy source is shut down, the temperature of the 3D micro-scale structure 110 will decrease to room temperature, with the molten hinges 104a-104c re-solidifying to their original phase and the shape of the self-folded structure 110 is maintained.

With the magnetic field energy source-based methods of the present disclosure, the induced magnetic field can be biocompatible and safe to use around, for example, living tissues and organs. Since the heat is only generate on the surface of the metal material of the panels 102a-102d, the temperature increase during the self-assembly process is only limited at the micro-scale structure or 2D net 100, which minimizes the possibility of harm to the surrounding environment. Further, where the selected material for the hinges 106a-106c has a relatively low melting point (e.g., PCL with a melting point on the order of about 60° C.), the low melting point of the hinges 106a-106c promotes the self-assembly to occur at a relatively low temperature, furthering improving biocompatibility of the process. Thus, the induction driven remote-controlled self-assembly methods of the present disclosure can be suitable for various biomedical applications (e.g., self-assembly is triggered in situ by locating the 2D net 100 within a body of the patient, and operating an induction coil outside of the patient's body to generate a magnetic field that passes through the patient's skin, tissue, etc., and interact with the 2D net 100 as described above) such a cell encapsulation, culture and organization, smart drug delivery, etc.

Embodiments and advantages of features of the present disclosure are further illustrated by the following non-limiting examples, but the particular materials and amounts thereof recited in these examples, as well as other conditions and details, should not be construed to unduly limit the scope of the present disclosure.

EXAMPLES

Microwave Energy Source

Example 1A

Testing was performed to evaluate the microwave energy source-based methods of the present disclosure. With reference to FIG. 4, to characterize the reflow of the material of the hinges 64 for self-assembly, 24 µm thick Megaposit™ SPR™ 220 photoresist hinge patterns were defined on a 20 nm thick Cr film (i.e., akin to the transition body 66 described above) deposited on top of a substrate comprised of a material that is inactive to microwaves (paper or glass, for example). Microwave energy from a commercialized 1050-watt magnetron (model number M24FA-410A available from Guangdong Galanz Enterprise Co, ltd., Guangdong Province, China) operating at a frequency of 2.45 GHz was then applied to the Cr film with different exposure times (0, 5, 10 and 15 seconds, respectively), and optical microscopic images were captured. FIGS. 10A-10D are the captured top view optical images at exposure times 0, 5, 10, and 15 seconds, respectively; FIGS. 10E-10H are the captured cross-sectional view optical images at exposure times 0, 5, 10, and 15 seconds, respectively. As shown in the top images (FIGS. 10A-10D) and the cross-section images (FIG. 10E-10H) of the SPR 220 hinges, the reflow of the hinges is clearly observable as the exposure (microwave radiation) time increases. In addition, the contact angle of the hinge decreases from 65° to 35°, indicating the level of reflow of the hinge material (FIGS. 10E-10H).

To quantitatively analyze the heat generation, inducing the hinge reflow by eddy current within the 20 nm thick Cr thin film, an infrared camera was used and recorded the surface temperature of the Cr thin film during the reflow process. The surface temperature of the 20 nm thick Cr thin film was found to rapidly and linearly increase from 28° C. (room temperature) to 177° C. in 15 seconds.

Figure 11A:
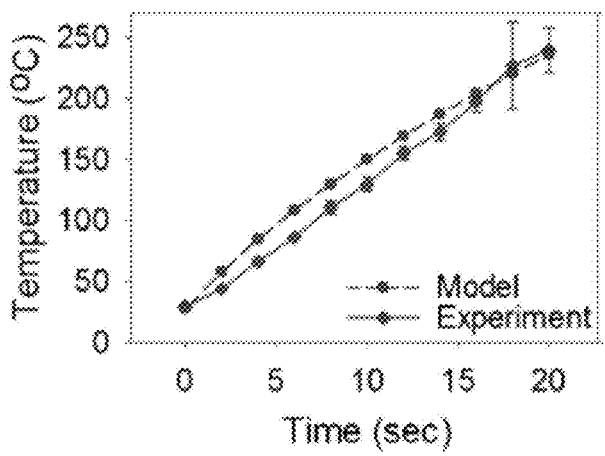
FIGS. 11A-11C are plots of measured and modeled data described in the Examples section.
Figure 11B:
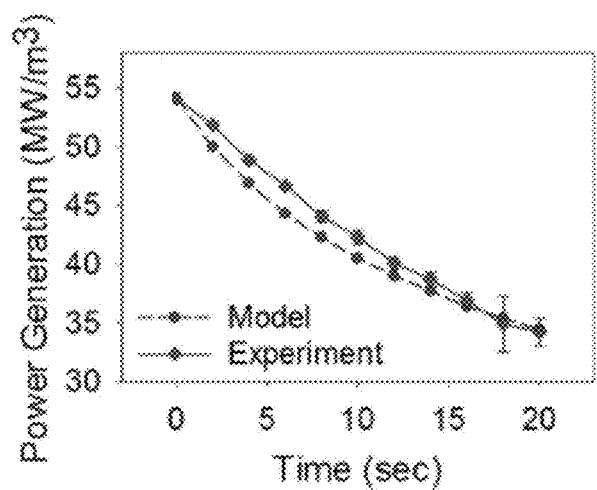
Figure 11C:
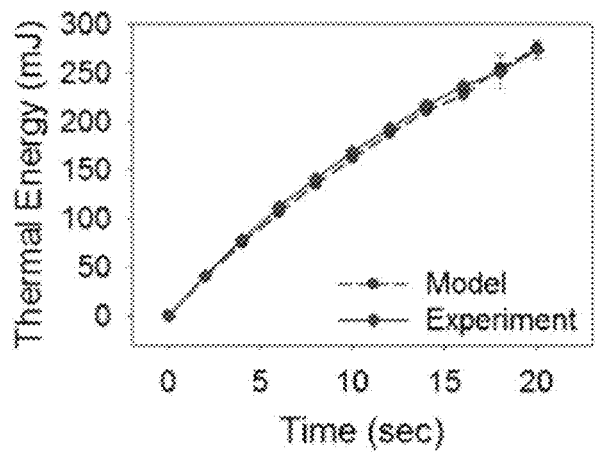

The heat generation within the Cr thin film under microwave radiation can be modeled by Faraday's law of induction and the definition of specific heat capacity. When an alternating magnetic field (B) is applied to a thin sheet of conductor (i.e., the 20 nm Cr film), a magnetic flux ($\Phi_B$=B× S, where S is the surface area of the conductor) is generated through the surface of the conductor. The time-varying magnetic flux is accompanied by an electric field (E, where $\nabla \times E = -\partial B/\partial t$), creating an eddy current (I), circulating in the Cr thin film against the resistance (R) of the thin metal film, which generates heat power (P) by Joule heating:

$$P = \frac{\pi^2 \cdot B_p^2 \cdot d^2 \cdot f^2}{6 \cdot \kappa \cdot \rho \cdot D} \quad (1)$$

where P is the heat power generation per unit mass, $B_p$ is the peak of magnetic field, d is the thickness of the conducting thin metal film, f is the frequency of the magnetic field, κ is a constant (κ=1 for thin sheet of conductor), ρ is the resistivity of the conducting thin metal film and D is the density of conducting thin metal film. From this model, when a constant P is generated, the temperature on the 20 nm Cr thin film was found to linearly increase with the increase of exposure time by $\Delta T = P \cdot t / C$, where $\Delta T$ is temperature changes, t is time, and C is specific heat capacity of the conducting material. FIG. 11A provides a comparison of surface temperature over time based on the model and the surface temperatures captured using the infrared camera. Temperatures obtained by the numerical modeling analysis shows a very good agreement with the experimental data obtained by the infrared camera. Similar comparisons between the numeric modeling of Equation (1) and the experimental data for heat power generation (P) over time, and thermal energy (Q=P×t) over time are presented in FIGS. 11B and 11C, respectively. It is noted that although a constant radiation power is applied from a magnetron, the heat power (P) generated from the metal film (FIG. 11B) decreased as exposure time increased. This is because the increased surface temperature leads to the increase of the resistivity ($\rho$) of the Cr thin film. Due to the resistivity changes, the heat power generation (P) decreases as time increases (FIG. 11B), and the thermal energy shows non-linear increases (FIG. 11C).

Example 1B

Figure 12A:
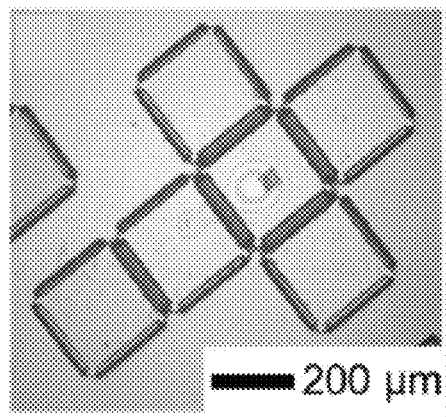
FIGS. 12A-12C are optical images of self-assembly of a 3D micro-scale structure described in the Examples section.
Figure 12B:
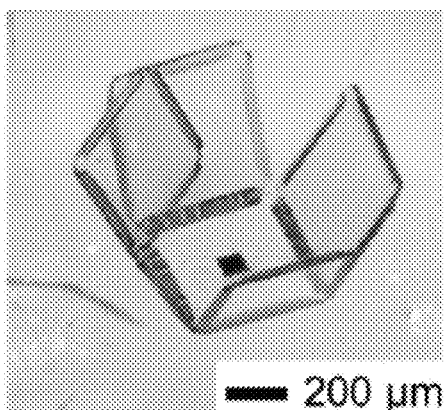
Figure 12C:
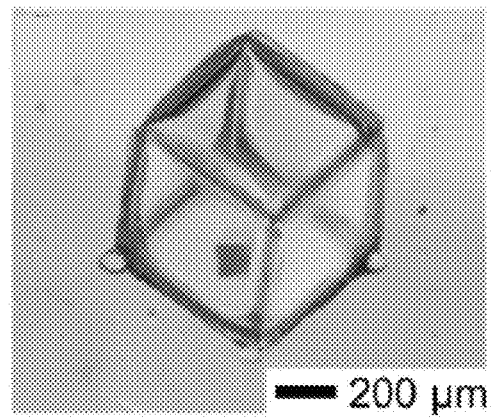

Provided as one illustrative example, to achieve 3D self-assembly of micro-scale structures using the heat generation from a nano-scale Cr thin film, a 20 nm thick Cr film was deposited on a 10×10 mm² glass substrate. 2D micro-scale nets (having the pattern of FIG. 1A) consisting of SU-8 micro-panels 22 and SPR 220 hinges 24 were fabricated over the Cr film. Then, the sample was exposed to microwave radiation at a frequency of 2.45 GHz. The samples were found to self-assemble in response to the applied microwaves. When the temperature of the hinges rose due to the heat generated from the Cr thin film and reached a temperature exceeding its melting point, the SPR 220 hinges were found to reflow and induce surface tension force to lift up the SU-8 panels, forming 3D micro-scale structures. Zoomed-in optical images of one of the samples during the self-assembly process are provided in FIGS. 12A-12C.

Example 1C

The folding angles of the 3D micro-scale structures of Example 1B (fabricated on a glass/Cr film substrate with a Cr film thickness of 20 nm) were captured at different exposure times. The folding of the cubic structure was found to start at about 6 seconds after microwave energy was applied, which reaches about 100° C. The structure was found to be totally folded to 90 degrees in 10 seconds. After the folding angle reached 90 degrees, even though microwave energy continued to be applied to the sample, the folding angle was found to remain at 90 degrees due to the interlocking between adjacent panels whose hinges have merged together.

Figure 13A:
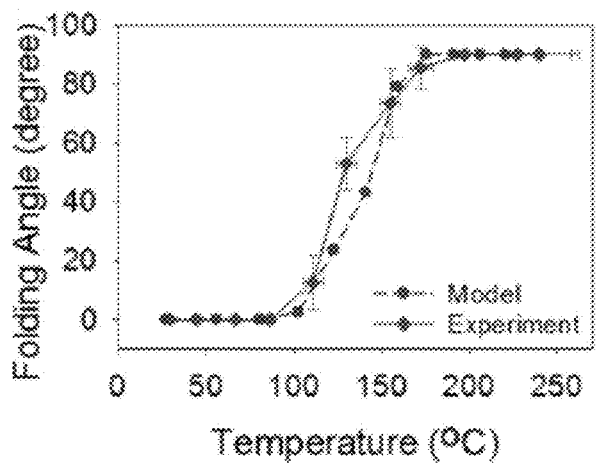
FIGS. 13A-13C are plots of measured and modeled data described in the Examples section.

To quantitatively analyze the assembly process, an equation of folding angles:

$$\theta = \frac{\alpha \cdot \pi^2 \cdot B_p^2 \cdot f^2 \cdot A \cdot d^3 \cdot (t - \beta)}{6 \cdot \kappa \cdot C \cdot \rho} \quad (2)$$

was derived from Equation (1) and $\Delta T = P \cdot t / C$, with an assumption that the folding angle is proportional to the heat generation P·t. In the equation, $\alpha$ is a constant of $2.7 \times 10^{-18}$ and the parameter, $\beta$, indicates the initial time that starts folding. FIG. 13A presents a comparison of folding angle as a function of temperature as experimentally obtained for the structure of Example 1B and the model of Equation (2).

Figure 13B:
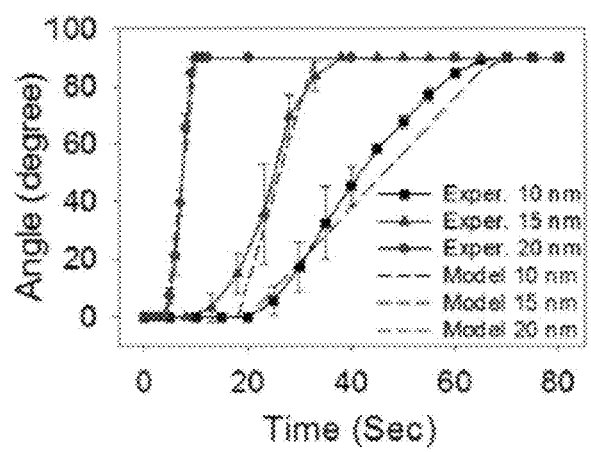
Figure 13C:
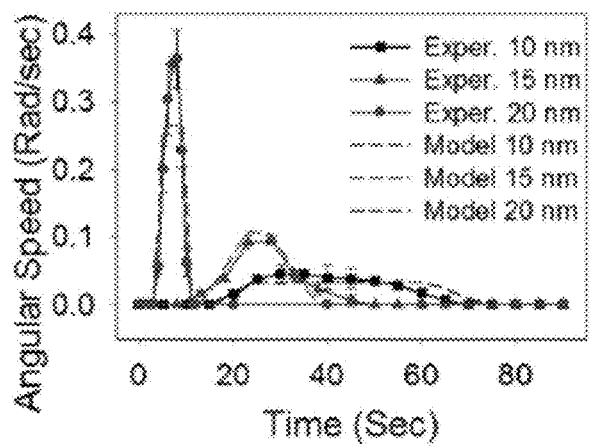

To further evaluate the model of Equation (2), a glass/Cr film substrate with a Cr thickness of 10 nm and a glass/Cr film substrate with a Cr thickness of 15 nm were prepared, and the 2D nets of Example 1B were fabricated on each of the glass/Cr film substrates. The samples were exposed to microwave radiation at a frequency of 2.45 GHz, causing the 2D nets to self-fold. The folding angles of the structures during the self-folding process were captured at different exposure times. FIG. 13B presents a comparison of folding angles over time for each of the experimental examples (examples using 10 nm thick Cr film, 15 nm thick Cr film, and 20 nm thick Cr film) and from the model of Equation (2). FIG. 13C presents a comparison of angular speed over time for each of the experimental examples and from the model of Equation (2). It was observed that the time (t) took to fold to $\theta = 90$ degrees significantly decreased as the thickness (d) of a Cr thin film increases due to the cubed term ($d^3$) in Equation (2). Thus, the time required to fold to a 90 degree folding angle significantly decreases as the thickness of the Cr film increases, resulting in high angular folding speeds. From Equation (2), the self-assembly of the 2D net was found to start at various times depending on the thickness (d) of the Cr thin film; a thicker Cr film results in an earlier initial folding time, while thinner Cr film results in a longer time (e.g., 10 nm: 6 seconds, 15 nm: 8 seconds, and 20 nm: 20 seconds). This can be explained as follows: the melting point of the SPR 220 photoresist hinge material is around 100° C., which means that the panels of the structure start to fold when the temperature reaches 100° C. Since the thicker Cr film generates higher heat energy, leading to an early time that is required to initiate folding and a faster temperature rise, the time for the surface temperature to reach 100° C. decreases.

Example 1D

Figure 14A:
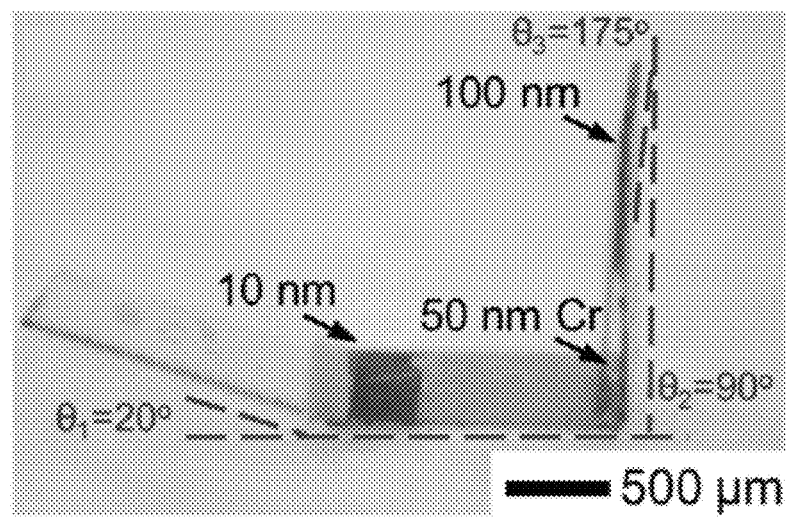
FIG. 14A is an optical image of a self-assembled 3D micro-scale structure described in the Examples section.
Figure 14B:
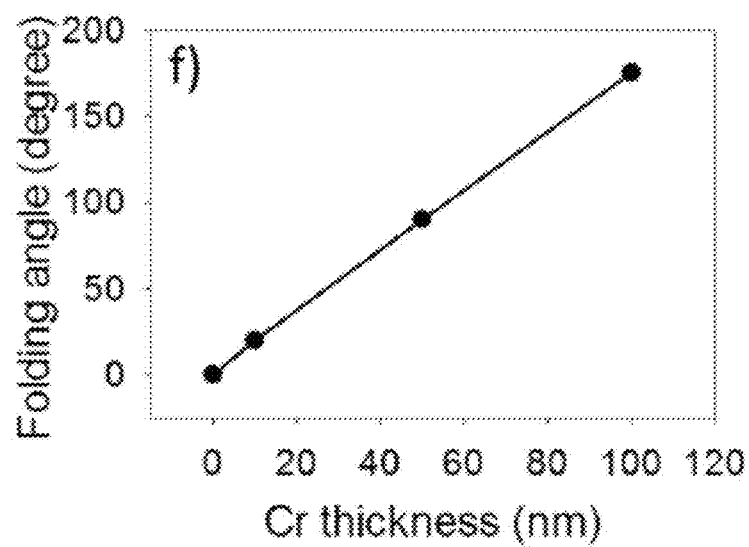
FIG. 14B is a plot of measure data described in the Examples section.

A 2D micro-scale net akin to FIG. 7A was fabricated on a substrate. The panels 62a-62d were formed as a continuous, homogenous body of SU-8 material, and the hinges 64a-64c were formed of PCL. The transition bodies 92a-92c were Cr films with different thicknesses. The first transition body 92a was a Cr film with a thickness of 10 nm; the second transition body 92b was a Cr film with a thickness of 50 nm; the third transition body 92c was a Cr film with a thickness of 100 nm. The 2D net structure was then released from the substrate and placed on paper. The 2D net structure was exposed to microwave radiation at a frequency of 2.45 GHz, causing the 2D net to self-fold. An image of the resultant 3D micro-scale structure was obtained, and the folding angles between the adjacent panels were estimated as shown in FIG. 14A. The determined folding angles as a function of Cr film thickness are reported in FIG. 14B. It was found that the Cr films with three different thicknesses generated different amounts of heat energy and triggered the self-assembly process with various folding angles. The hinge adjacent to the 10 nm thick Cr film pattern showed the smallest folding angle of 20 degrees while the hinges adjacent to the 50 nm thick Cr film and the 100 nm thick Cr film patterns have folding angles of 90 degrees and 175 degrees, respectively. This result demonstrates that complex microstructures with diverse folding configurations can thus be realized by applying multiple metal thicknesses around the hinges. Since the folding angles of the panels are proportional to the heat generation within the Cr film and the heat generation largely depends on the Cr film thickness (unless the thickness exceeds its skin depth, about 3 μm at 2.46 GHz), it is possible to realize self-assembly of 3D micro-scale structures with different folding angles by locally applying different thicknesses of Cr film on multiple hinge areas. The increase in the Cr film thickness results in an increased heat generation, leading to a higher temperature and a larger folding angle. The multiple metal thicknesses around the hinges also allows the folding of each panel pair to start at a different time, resulting in a sequential self-folding pattern. The ability of self-assembly with multiple folding angles and sequential folding, resulting in complex 3D micro-scale structures, could largely enhance the capability of the 3D micro-scale structures for various applications such as micro-actuators, microrobots and 3D microoptics.

Magnetic Field Energy Source

With the examples described below, various samples were energized by an indication system. The induction system included an induction coil made of copper wire with a diameter of 1 mm; the induction coil consisted of 8 turns of the copper wire, had a diameter of 1 cm, and a length of 1.5 cm. The induction coil was connected to a high frequency induction circuit that was powered by a power supply with a maximum power of around 200 W. The copper coil and induction circuit operated to generate a time-dependent magnetic field with a frequency of 5 MHz. A water-cooling system was also provided with the induction system, and operated to deliver water at a temperature of 10° C. to an environment of the induction coil. Unless otherwise noted, with each test, the sample in question was placed on top of piece of paper directly above the induction coil, and was centered relative to the induction coil.

Example 2A

Testing was performed to evaluate the magnetic field energy source-based methods of the present disclosure. To analyze the heat generation of a nickel thin film useful as a material of a panel of a 2D net (e.g., the panels 22 of the 2D net 20 of FIG. 1A), surface temperatures of nickel thin films under various induction radiation times were monitored and characterized using an optical microscope and an infrared camera (Seek™ Thermal CompactPro thermal camera from Seek Thermal, Inc.). Sample panels comprising a nickel thin film with dimensions of 500 μm×500 μm and a thickness of 15 μm were prepared (Ni Sample Panel 1). The Ni Sample Panel 1 was placed on the induction coil of the induction system, and the induction system was operated to deliver an induction input power of 200 W. A temperature of the Ni Sample Panel 1 was taken at the same point on the surface of the Ni Sample Panel 1 at 0, 10, 30 and 60 seconds from the start of operation of the induction system, and were calibrated using a thermocouple to obtain an accurate temperature reading. The surface temperature was found to increase from 19° C. (water cooling temperature) to 50° C. within 60 seconds while the atmospheric temperature (or temperature of the environment of the panel undergoing testing) remained the same. It was surmised from these results that at the same induction power (P), the increase of time (t) leads to the increase of induction heat generation (W=P·t), resulting in a higher surface temperature of the thin film Ni panel.

Example 2B

To verify the reliability of the temperature measurements of Example 2A, simulations of the surface temperatures of Ni thin films under induction radiations were conducted using COMSOL Multiphysics. To simplify the simulation process, the Ni Sample Panel 1 was replaced with an Ni thin film plate with the sample total surface area in the simulator. The Ni plate was placed on a paper substrate above the induction coil. Actual coil temperatures were monitored during the assembly process and then applied to the coil in the simulator. It was found that the surface temperatures of the Ni plates increased from 18° C. to 58° C., which agrees well with the temperature measurements of Example 2A. The slight difference between the simulated and measured data may be due to the shape difference between the Ni Sample Panel 1 and the Ni plates, and the variations of induction frequency and power in the measured data.

Example 2C

To quantitatively analyze the temperatures on the surface of the Ni panels, additional sample panels were prepared as follows: Sample panels comprising a nickel thin film with dimensions of 500 μm×500 μm and a thickness of 5 μm (Ni Sample Panel 2) were prepared, and sample panels comprising nickel thin film with dimensions of 500 μm×500 μm and a thickness of 1 μm (Ni Sample Panel 3) were prepared. Each of Ni Sample Panels 1, 2 and 3 were placed on the induction coil of the induction system, and the induction system was operated to deliver an induction input power of 120 W for a 60 second test period during which the surface temperature of the Ni Sample Panel being tested was measured using an infrared camera.

Figure 15A:
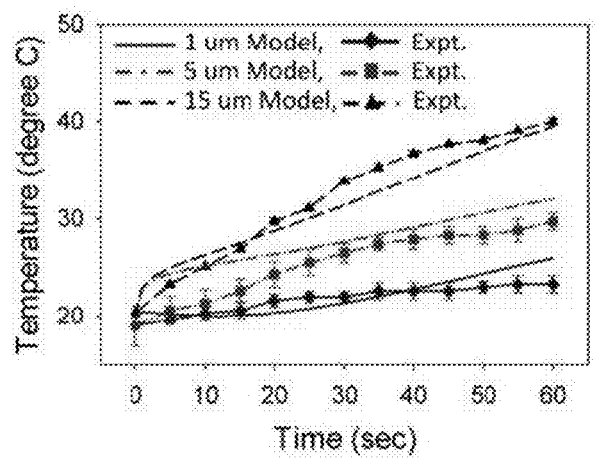
FIGS. 15A-15C are plots of measured and modeled data described in the Examples section.

Heat generation under the test conditions for Ni Sample Panels 1, 2, and 3 was also modeled using Equation (1). In the context of induction driven self-assembly, the terms of Equation (1) are: P is the eddy current power dissipation per unit mass, $B_p$ is the magnetic field strength, d is the thickness of the conductor, f is the frequency of the magnetic field, κ is a constant (κ=1 for thin sheet of metal; κ=2 for a thin metal wire), ρ is the electrical resistance of the conductor, and D is the density of the conductor. The measured and modeled results for Example 2C are reported in FIG. 15A. As indicated in Equation (1), when the thickness (d) of the thin metal film increases, the power dissipation (P) by eddy current increases, leading to an increase of temperature on the surface of the thin film. As expected, the 15 μm thick Ni sample (Ni Sample Panel 1) reached the highest temperature (40° C.) at 60 seconds, while the 5 μm (Ni Sample Panel 2) and 1 μm (Ni Sample Panel 3) thick Ni samples reached temperatures of 30° C. and 25° C., respectively.

Example 2D

Figure 15B:
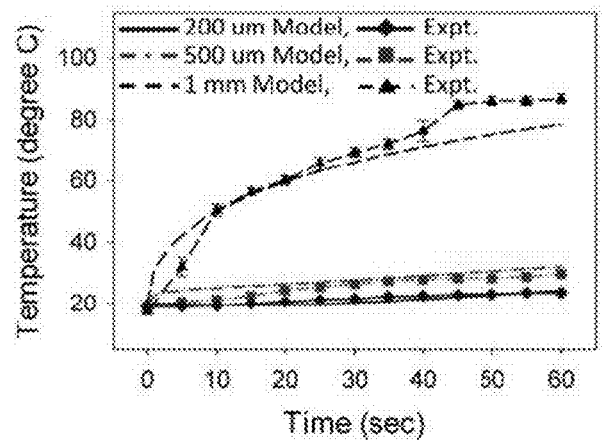

To further quantitatively analyze the temperatures on the surface of the Ni panels, additional sample panels were prepared as follows: Sample panels comprising a nickel thin film with dimensions of 200 μm×200 μm and a thickness of 15 μm (Ni Sample Panel 4) were prepared, and sample panels comprising nickel thin film with dimensions of 1000 μm×1000 μm and a thickness of 15 μm (Ni Sample Panel 5) were prepared. Each of Ni Sample Panels 1, 4 and 5 were placed on the induction coil of the induction system, and the induction system was operated to deliver an induction input power of 120 W for a 60 second test period during which the surface temperature of the Ni Sample Panel being tested was measured using an infrared camera. Heat generation under the test conditions for Ni Sample Panels 1, 4, and 5 was also modeled using Equation (1). The measured and modeled results for Example 2D are reported in FIG. 15B. It was determined that the surface temperature decreases with the decrease in panel size. As indicated by Equation (1), the power (P) of induction increases when the area (A) of the thin metal film increases, leading to a high heat generation (W), thus a high surface temperature.

Example 2E

Figure 15C:
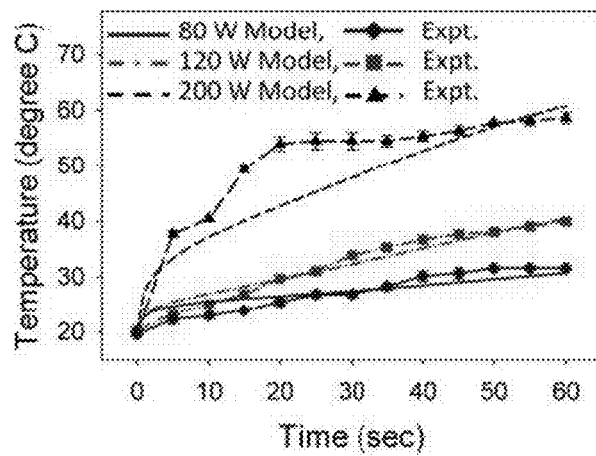

To further quantitatively analyze the temperatures on the surface of the Ni Panels, test panels of Ni Sample Panel 2 were subjected to differing induction powers. Each of the Ni Sample Panels 2 were placed on the induction coil of the induction system, and the induction system was operated to deliver an induction input power of 80 W (test 1), 120 W (test 2), or 200 W (test 3) for a 60 second test period during which the surface temperature of the Ni Sample Panel being tested was measured using an infrared camera. Heat generation under the conditions of test 1, test 2, and test 3 for Ni Sample Panel 2 was also modeled using Equation (1). The measured and modeled results for Example 2E are reported in FIG. 15C. It was found that the intensity (B) of the magnetic field is induced by the induction coils is directly proportional to the input power of the induction circuits. A higher induction input power results in a higher magnetic field intensity (B), which leads to a high eddy current power dissipation (P), as indicated by Equation (1). The high eddy current power dissipation (P) causes a large heat generation and an increase of the surface temperature of the Ni thin film panel. In FIG. 15C, a highest surface temperature of 60° C. was observed with the input power of 200 W (test 3), while the highest surface temperature of the 80 W (test 1) and 120 W (test 2) input powers were 30° C. and 40° C., respectively.

For all of the temperature experiments of Examples 2C-2E, the surface temperature of the Ni sample panel increases with an increase of induction radiation time, which can be explained by the heat generation equation W=P·t. Also, it can be observed from FIGS. 15A-15C that the temperature increase begins to saturate at high temperature. This is due to the high conductive and convective heat loss of the Ni panels at a high temperature. All the modeling of Examples 2C-2E was found to agree well with the experimental temperature data.

Example 2F

A sample 2D net with the pattern of FIG. 1A and comprising Ni panels and PCL hinges was prepared. In particular, the sample preparation began with a glass substrate. A 10 nm chromium (Cr) adhesion layer and a 300 nm copper (Cu) sacrificial layer were deposited on the glass substrate using electron beam (E-beam) evaporation. A 30 nm thick aluminum oxide ($Al_2O_3$) layer was patterned onto the Cu layer using photolithography, E-beam evaporation, and lift-off process. The purpose of the $Al_2O_3$ layer was to support an entirety of the completed net structure subsequently formed on top of the $Al_2O_3$ layer and to prevent the subsequently-formed panels from falling apart. A 100 nm nickel (Ni) layer was patterned over the $Al_2O_3$ layer using photolithography, E-beam evaporation, and lift-off process. The Ni patterns were slightly larger than the $Al_2O_3$ patterns so that the Ni was in contact with the Cu layer. The purpose of the Ni pattern was to provide a seed layer for Ni panel electroplating. Ni panels of 500 μm×500 μm were patterned on the thin Ni layer using Ni electroplating to a thickness of 20 μm. The Ni electroplating solution used was Nickel Sulfamate RTU from Technic, Inc. A pattern of hinges were formed between immediately adjacent ones of the Ni panels by a photoresist film available from MicroChem Corp. of Newton, Mass. under the trade designation Megaposit™ SPR™ 220, with the hinge material exposed and developed with an AZ® Developer from MicroChemicals GmbH. A PCL solution (mixture of PCL (average Mn 80 000, obtained from Sigma Aldrich) and 1,1,2,2-Tetrachloroethane [$Cl_2CHCHCl_2$] (obtained from Sigma Aldrich)) was spin coated on the sample. A razor blade was used to scrape through the sample to remove the excess PCL on the SPR 22 photoresist. The solvent in the PCL solution was evaporated in a vacuum chamber for 1 hour to achieve a solid layer of PCL. An oxygen ($O_2$) plasma was used to remove the top layer of the PCL and expose the SPR 220 photoresist. A lift-off process with the AZ® Developer was used to remove the SPR 220 photoresist and leave the PCL hinges between immediately adjacent ones of the Ni panels. The sample was then submerged in a Cu etchant (APS100™ Copper Etchant from Transene Company, Inc.) to release the 2D net from the glass substrate. The 2D net was then transferred to a paper substrate.

Figure 16A:
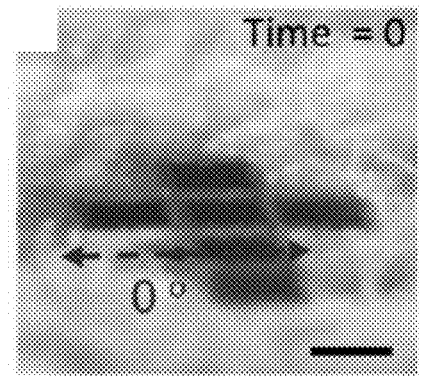
FIGS. 16A-16D are optical images of self-assembly of a 3D micro-scale structure described in the Examples section.
Figure 16B:
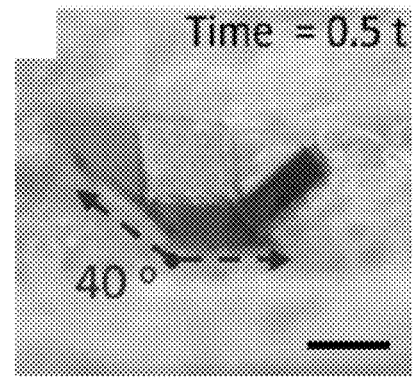
Figure 16C:
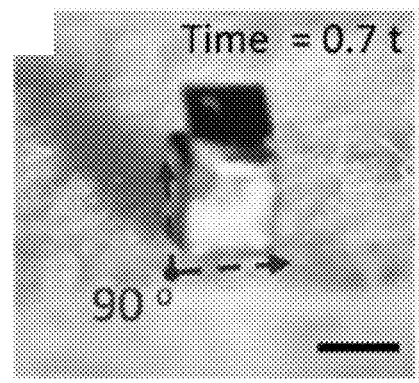
Figure 16D:
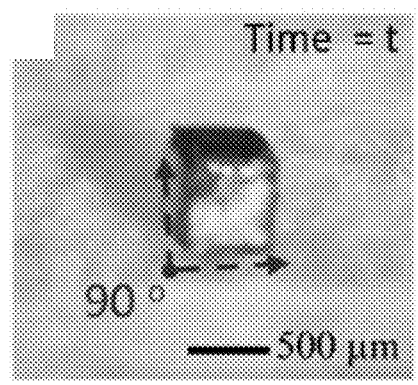

The sample 2D net of Example 2F, supported by the paper substrate, was placed on the induction coil of the induction system. The induction system was operated to deliver an induction input power of 200 W, and the structure was monitored using a microscope and recorded using an optical camera. FIG. 16A is an optical image of the sample 2D net at the start of the delivery of induction input power. In response to the induction input power, the 2D net began to self-fold, ultimately resulting in a 3D micro-scale structure. FIGS. 16B-16D are optical images of the folding process. It was observed that the folding of the Ni panels started when the surface temperate of the Ni exceeded the melting point of the PCL hinges (around 60° C.). Under the induction radiation, the surface temperature of the Ni continued to increase, which resulted in further melting of the PCL hinges and leading to the completely folded 3D structure. It was observed that the "top" panel of the resultant cubic structure showed slower folding behavior as compared to the other panels (as exhibited, for example, by the state of FIG. 16C) due to the higher position of the top panel above the induction coil, leading to a weaker magnetic field and thus less heat generation.

Figure 17A:
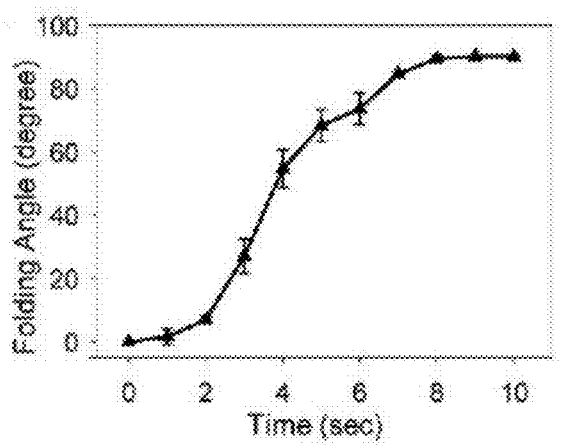
FIGS. 17A-17C are plots of measured data described in the Examples section.
Figure 17B:
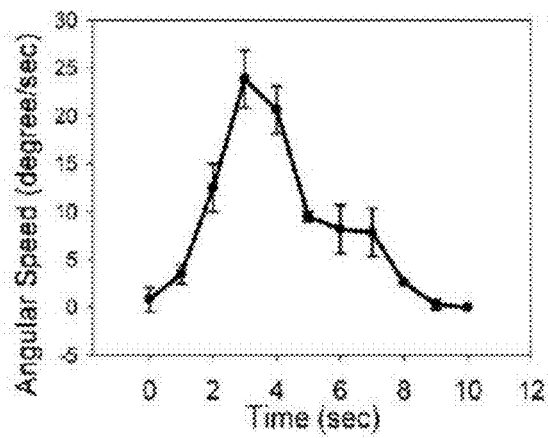
Figure 17C:
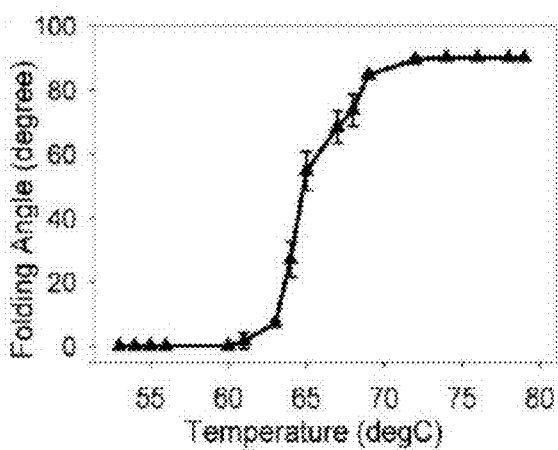

As noted in FIGS. 16A-16D, the folding angle and angular folding speed of two the Ni panels relative to one another at various points in time was captured and plotted; the surface temperature of the Ni panels was measured using an infrared camera. FIG. 17A is a plot of the recorded folding angle over time. It was observed that the folding angle of the Ni panels increased from 0 degrees to 90 degrees in 10 seconds, which indicates that a totally assembled 3D micro-scale structure can be achieved in under 10 seconds. FIG. 17B is a plot of the recorded angular folding speed over time. It was observed that the folding speed of the Ni panels initially increased with the increase of induction radiation time due to the constant increase in Ni panel surface temperature. As the panels continued to fold up (i.e., away from the induction coil), the amount of heat generated was reduced because of the weaker magnetic field at the higher position, leading to a decrease in folding speed. A maximum folding speed of 25 degrees/sec was achieved at the induction radiation time of 4 seconds. The folding speed continued to decrease to 0 when the folding angle reached 90 degrees. FIG. 17C is a plot of the recorded folding angle at corresponding recorded surface temperature. It was observed that the folding angle of the panels remained at 0 degrees until the surface temperature of the panels reached 60° C. (the melting point of PCL). After the folding angle reached 90 degrees, the increase of surface temperature did not affect the folding angle due to the locking mechanism of the hinges and the panels. The measured folding angle at different temperatures (FIG. 17C) agrees well with the folding angle measurement at different radiation times (FIG. 17A).

Example 2G

Figures 18A, 18B, 18C:
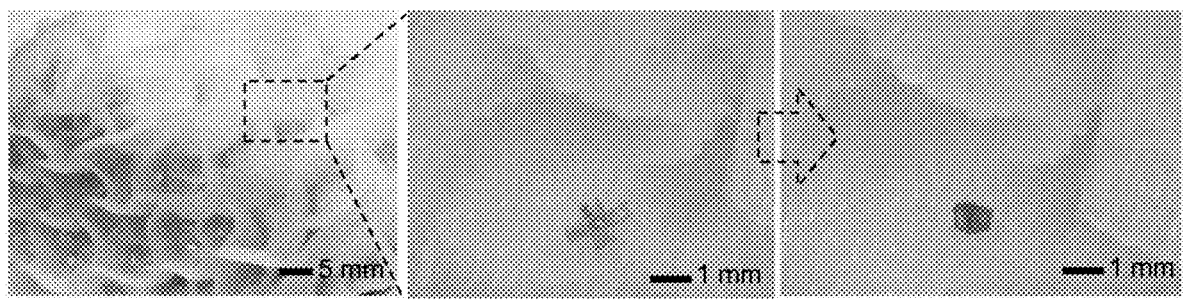
FIGS. 18A-18C are optical images of self-assembly of a 3D micro-scale structure while in contact with a section of reticulum beef tripe described in the Examples section.

A sample 2D net with the pattern of FIG. 1A and comprising Ni panels and PCL hinges was prepared as described in Example 2F. The 2D net was placed in a section of reticulum beef tripe (i.e., the paper substrate of Example 2F was replaced by a section of beef tripe) as shown by the images of FIGS. 18A and 18B. The beef tripe supporting the sample 2D net of Example 2G was placed on the induction coil of the induction system. The induction system was operated to deliver an induction input power of 200 W, and the structure was monitored using a microscope and recorded using an optical camera. The water-cooling assembly provided with the induction system was operated to keep the temperature of the induction coil as well as the environment at a temperature of approximately 20° C. It was observed that the magnetic field generated by the induction coil penetrated through the beef tripe and reached the 2D net. Eddy current created inside the Ni panels of the 2D net generated heat energy sufficient to melt the PCL hinges; it was observed that the 2D net self-folded into a 3D micro-scale structure (cubic structure) as shown by the image of FIG. 18C. Infrared images were obtained throughout the self-folding process. It was observed that the surface temperature of the beef tripe was about 10° C. (due to its refrigerated storage condition prior to the experiment). The surface temperature of the 2D net prior to the delivery of induction input power was about 25° C. (room temperature). During the self-assembly process, it was observed that the surface temperature of the 2D net increased to around 60° C. while the surface temperature of the beef tripe did not change.

The results of Example 2G indicate that the induction magnetic field was able to penetrate through a biomaterial (beef tripe); self-assembly was triggered remotely without touching or seeing the sample to be assembled. Further, the heat generation was localized only at the 2D net and presented minimal potential harm to the biomaterial.

Example 2H

Figures 19A, 19B, 19C:
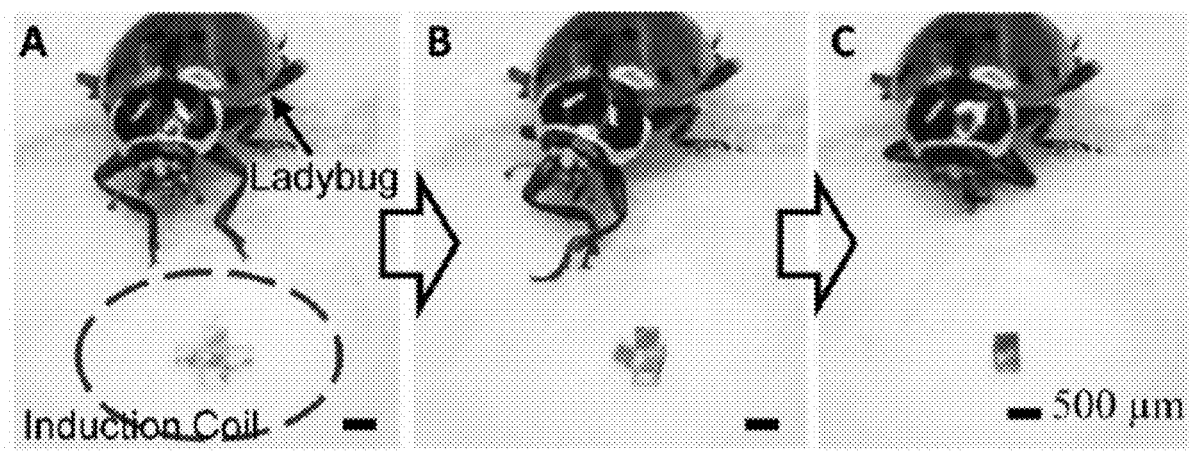
FIGS. 19A-19C are optical images of self-assembly of a 3D micro-scale structure proximate a ladybug described in the Examples section.
Figure 20A:
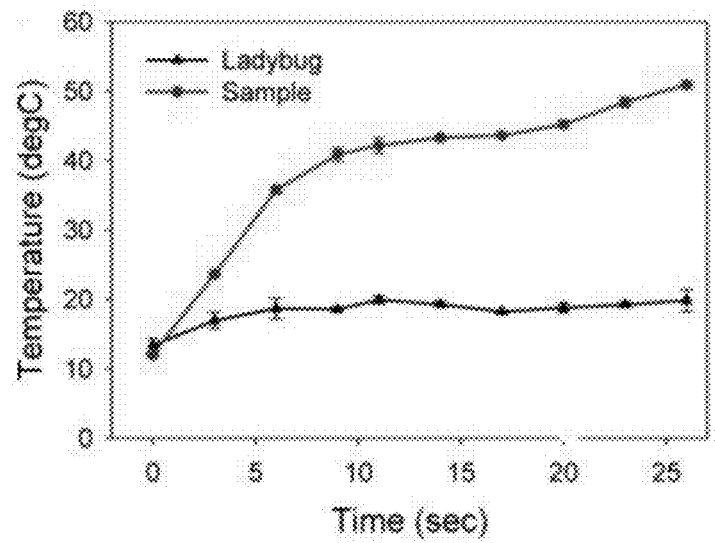
FIGS. 20A and 20B are plots of measure data described in the Examples section.
Figure 20B:
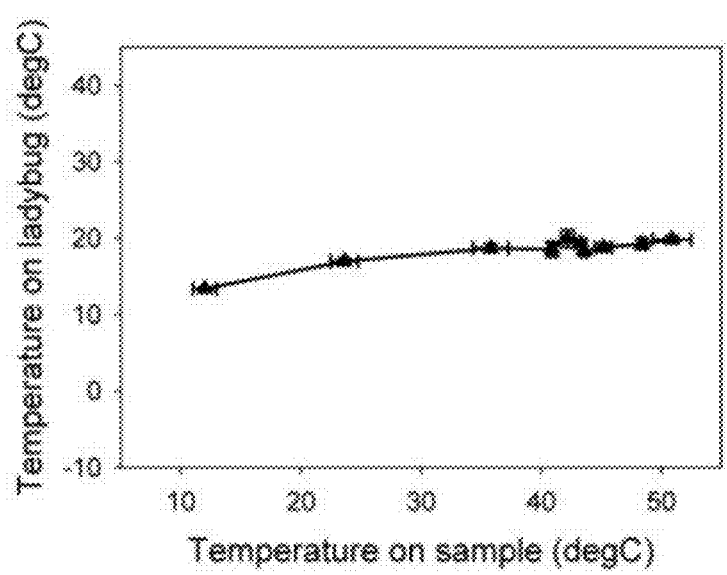

A sample 2D net with the pattern of FIG. 1A and comprising Ni panels and PCL hinges was prepared as described in Example 2F. The 2D net was placed on a paper substrate that in turn was placed on the induction coil of the induction system. A live ladybug was placed on the paper substrate in close proximity to the 2D net. The induction system was operated to deliver an induction input power of 200 W, and the structure was monitored using a microscope and recorded using an optical camera. It was observed that the 2D net was triggered to self-assemble into a 3D micro-scale structure (cubic structure). FIGS. 19A-19C are optical images at various points in time during the experiment, and show the 2D net (FIG. 19A) self-assembling to the 3D micro-scale structure (FIG. 19C). It was observed that the ladybug remained undisturbed during the self-assembly process, indicating that the heat generation for the self-assembly was localized at the sample and did not affect the ladybug. The surface temperature of the sample and the ladybug during the self-assembly process were recorded with an infrared camera, and showed that the surface temperature of the ladybug remained the same while the sample temperature increased from 20° C. to about 60° C. during the self-assembly process. The recorded surface temperatures of the sample and the ladybug over time during the experiment are reported in FIG. 20A. As shown, the surface temperature of the ladybug remained at about 20° C. during the self-assembly process, whereas the surface temperature of the sample increased from 12° C. to 54° C. in 25 seconds. FIG. 20B plots the surface temperature of the ladybug at different surface temperatures of the sample during the experiment. The straight line of FIG. 20B indicates that the heat generated by the Ni panels of the sample did not affect the ladybug.

The results of Example 2H further indicates that the localized heat of induction-driven self-assembly limits the damage of heat to living tissues and organs. The induction-based self-assembly methods of the present disclosure are suitable for biomedical applications such as drug delivery systems, cell capture, cell encapsulation, etc.

The present disclosure provides a marked improvement over previous designs and techniques. Micro-scale 2D nets can be remotely or indirectly triggered to self-assemble into a 3D micro-scale structure, for example by causing localized heating sufficient to melt hinges of the 2D net. In some embodiments, microwave energy is utilized as a triggering source, generating an eddy current inside one or more components of the 2D net (e.g., a thin film metal) that in turn generate heat. In other embodiments, magnetic field energy is utilized as a triggering source, generating eddy current inside one or more components of the 2D net (e.g., a metal panel of the 2D net) that in turn generate heat. No physical contact is needed to trigger the folding process, which increases the manipulative ability of the self-assembly process. The self-assembly process can be easily and precisely controlled by tuning the reaction time of the microwave energy as well as the thickness of the conducting thin film. The remote-controlled self-assembly methods and corresponding structures of the present disclosure are suitable for diverse applications like microbots, 3D sensors, and 3D metamaterials, biomedical applications, etc.

Although the present disclosure has been described with reference to preferred embodiments, workers skilled in the art will recognize that changes can be made in form and detail without departing from the spirit and scope of the present disclosure.

What is claimed is:

1. A method of manufacturing a 3D micro-scale structure, the method comprising:
   providing a 2D net including a plurality of panels, a plurality of hinges and at least one transition body, wherein the panels are arranged in a pattern, and further wherein respective ones of the hinges extend between and interconnect immediately adjacent ones of the panels within the pattern;
   powering an energy source remote from the 2D net to deliver energy to the 2D net and trigger the 2D net to self-fold into a 3D micro-scale structure;
   wherein the delivered energy creates an eddy current within the at least one transition body;
   wherein the eddy current generates heat at the at least one transition body sufficient to melt at least one of the plurality of hinges while each of the plurality of panels remains rigid;

wherein the at least one melting hinge causes the corresponding panels associated with the at least one melting hinge to fold relative to one another;

wherein the plurality of hinges includes a first hinge and a second hinge, the first hinge being apart from the second hinge and interconnecting a pair of the panels differing from a pair of the panels interconnected by the second hinge, wherein the at least one transition body includes a first transition body in direct contact with the first hinge and a second transition body in direct contact with the second hinge; and wherein the step of powering includes generating heat at the first transition body differing from heat generated at the second transition body.

2. The method of claim 1, wherein the energy source is a microwave energy source.

3. The method of claim 2, wherein the delivered energy is electromagnetic waves.

4. The method of claim 2, wherein the at least one transition body is a thin metal film.

5. The method of claim 4, wherein the thin metal film is made of chromium.

6. The method of claim 2, wherein the at least one transition body comprises a plurality of thin metal films, respective ones of the thin metal films being in contact with a corresponding one of the plurality of hinges.

7. The method of claim 2, wherein a melting point of each of the plurality of panels is higher than a melting point of each of the plurality of hinges.

8. The method of claim 1, wherein the delivered energy is a magnetic field.

9. The method of claim 8, wherein the energy source includes an induction coil.

10. The method of claim 9, wherein the energy source generates a time-dependent magnetic field.

11. The method of claim 8, wherein the at least one transition body is a metal component of at least one of the plurality of panels.

12. The method of claim 11, wherein the at least one transition body includes a metal component of each of the plurality of panels.

13. The method of claim 12, wherein each of the plurality of panels comprises a nickel material.

14. The method of claim 8, wherein the 2D net is located within a human patient, and further wherein the delivered energy travels through tissue of the patient.

15. The method of claim 8, wherein a melting point of each of the plurality of hinges is not greater than 60° C.

16. The method of claim 1, wherein the at least one transition body comprises a single transition body in direct contact with each of the plurality of hinges.

17. The method of claim 16, wherein the single transition body is encapsulated between the plurality of panels and a support layer.

18. The method of claim 1, wherein the step of powering includes inducing a fold angle at the first hinge differing from a fold angle induced at the second hinge.

* * * * *